(12) United States Patent
Shiba et al.

(10) Patent No.: US 10,492,682 B2
(45) Date of Patent: Dec. 3, 2019

(54) OPHTHALMIC ANALYSIS DEVICE AND OPHTHALMIC ANALYSIS PROGRAM

(71) Applicant: NIDEK CO., LTD., Gamagori, Aichi (JP)

(72) Inventors: Ryosuke Shiba, Gamagori (JP); Norimasa Satake, Nukata (JP); Tetsuya Kano, Toyota (JP); Yasuhiro Furuuchi, Gamagori (JP); Yuki Kuno, Gamagori (JP); Ai Takaya, Hamamatsu (JP); Naoki Takeno, Gamagori (JP); Yukihiro Higuchi, Toyota (JP); Hajime Namiki, Gamagori (JP)

(73) Assignee: NIDEK CO., LTD., Gamagori (JP)

( * ) Notice: Subject to any disclaimer, the term of this patent is extended or adjusted under 35 U.S.C. 154(b) by 296 days.

(21) Appl. No.: 15/297,523

(22) Filed: Oct. 19, 2016

(65) Prior Publication Data
US 2017/0112377 A1 Apr. 27, 2017

(30) Foreign Application Priority Data

Oct. 21, 2015 (JP) .................. 2015-207571
Oct. 21, 2015 (JP) .................. 2015-207572

(51) Int. Cl.
*A61B 3/14* (2006.01)
*A61B 3/10* (2006.01)
(Continued)

(52) U.S. Cl.
CPC .......... *A61B 3/1233* (2013.01); *A61B 3/0025* (2013.01); *A61B 3/0058* (2013.01);
(Continued)

(58) Field of Classification Search
CPC .......... A61B 3/103; A61B 3/14; A61B 3/113; A61B 3/1225; A61B 3/024; A61B 3/032; A61B 3/18; A61B 3/1015
(Continued)

(56) References Cited

U.S. PATENT DOCUMENTS

2008/0007693 A1 1/2008 Williams et al.
2012/0218517 A1 8/2012 Imamura
(Continued)

FOREIGN PATENT DOCUMENTS

JP 2008-073280 A 4/2008
JP 2013-202298 A 10/2013
(Continued)

OTHER PUBLICATIONS

Reif, Roberto et al. "Quantifying Optical Microangiography Images Obtained From a Spectral Domain Optical Coherence Tomography System". Hindawi Publishing Corporation International Journal of Biomendical Imaging, vol. 2012, Article ID 509783, pp. 1-11, 2012.
(Continued)

*Primary Examiner* — Dawayne Pinkney
(74) *Attorney, Agent, or Firm* — Oliff PLC

(57) ABSTRACT

An ophthalmic analysis device for analyzing OCT motion contrast data including blood vessel information of a subject eye acquired by an ophthalmic OCT, includes: a processor; and memory storing computer readable program, when executed by the processor, causing the ophthalmic analysis device to execute: an analysis process of analyzing the OCT motion contrast data to acquire a measurement result related to a capillary area of the subject eye. The analysis process executes an alleviating process for alleviating the influence of great blood vessels having blood vessel diameters larger than those of capillaries on the measurement result to acquire the measurement result related to the capillary area.

22 Claims, 13 Drawing Sheets

(51) Int. Cl.

| | | |
|---|---|---|
| *A61B 3/02* | (2006.01) | |
| *A61B 3/00* | (2006.01) | |
| *A61B 3/12* | (2006.01) | |
| *G06T 7/00* | (2017.01) | |
| *G06T 7/20* | (2017.01) | |
| *G06K 9/00* | (2006.01) | |
| *G06T 7/11* | (2017.01) | |
| *G06T 7/60* | (2017.01) | |
| *G06T 7/90* | (2017.01) | |
| *G06T 7/579* | (2017.01) | |
| *G06T 11/60* | (2006.01) | |

(52) U.S. Cl.
CPC ............ *A61B 3/102* (2013.01); *A61B 3/1241* (2013.01); *G06K 9/0061* (2013.01); *G06T 7/0012* (2013.01); *G06T 7/11* (2017.01); *G06T 7/20* (2013.01); *G06T 7/579* (2017.01); *G06T 7/60* (2013.01); *G06T 7/90* (2017.01); *G06T 11/60* (2013.01); *G06T 2207/30041* (2013.01); *G06T 2207/30101* (2013.01)

(58) Field of Classification Search
USPC ....... 351/206, 200, 205, 209, 210, 221–223, 351/245–246
See application file for complete search history.

(56) References Cited

U.S. PATENT DOCUMENTS

| | | |
|---|---|---|
| 2012/0236259 A1 | 9/2012 | Abramoff et al. |
| 2013/0301008 A1 | 11/2013 | Srivastava et al. |
| 2014/0221827 A1 | 8/2014 | Motaghiannezam et al. |
| 2014/0276025 A1* | 9/2014 | Durbin ................. A61B 5/4842 600/427 |
| 2014/0357990 A1* | 12/2014 | Wang ................... A61B 5/0261 600/425 |
| 2015/0168127 A1 | 6/2015 | Takeno et al. |
| 2015/0313466 A1 | 11/2015 | Yoshida |
| 2016/0302738 A1 | 10/2016 | Yoshida et al. |
| 2016/0310024 A1 | 10/2016 | Yoshida et al. |
| 2017/0035286 A1* | 2/2017 | Meyer ................... A61B 3/102 |
| 2018/0172426 A1 | 6/2018 | Takeno et al. |
| 2019/0059718 A1 | 2/2019 | Abramoff et al. |

FOREIGN PATENT DOCUMENTS

| | | |
|---|---|---|
| JP | 2014-504523 A | 2/2014 |
| JP | 2015-131107 A | 7/2015 |
| WO | 2013-137148 A1 | 9/2013 |

OTHER PUBLICATIONS

Yali Jia, et al. "Quantitative Optical Coherence Tomography Angiography of Choroidal Neovascularization in Age-Related Macular Degeneration", Ophthalmology, vol. 121, No. 7, Jul. 1, 2014, pp. 1435-1444.

Mar. 7, 2017 Search Report issued in European Patent Application No. 16194794.0.

Yi-Sing Hisiao. et al., Measurements on Vessel Length Density and Fovea Avascular Zone Area with OCT-Angiography: a Repeatability Study using AngioVue, Investigative Ophthalmology & Visual Science, U.S.A., Jun. 2015, vol. 56, p. 1646.

Jul. 2, 2019 Office Action issued in Japanese Patent Application No. 2015-207571.

Jul. 2, 2019 Office Action issued in Japanese Patent Application No. 2015-207572.

\* cited by examiner

OPHTHALMIC ANALYSIS DEVICE AND OPHTHALMIC ANALYSIS PROGRAM

CROSS REFERENCE TO RELATED APPLICATION

This application is based upon and claims the benefit of priorities of Japanese Patent Application No. 2015-207571 filed on Oct. 21, 2015 and Japanese Patent Application No. 2015-207572 filed on Oct. 21, 2015, the contents of which are incorporated herein by reference in its entirety.

BACKGROUND

The present invention relates to an ophthalmic analysis device and an ophthalmic analysis program for analyzing subject eye data including blood vessel information of a subject eye.

Nowadays, a technology for obtaining motion contrast data of a subject eye by an OCT technology receives attention (see Non-Patent Literature 1).

[Non-Patent Literature 1] Roberto Reif et al. "Quantifying Optical Microangiography Images Obtained from a Spectral Domain Optical Coherence Tomography System", International Journal of Biomedical Imaging, Vol. 2012, Article ID 509783, p. 11

SUMMARY

However, although various improvements are being made with respect to imaging of motion contrast data, with respect to analyzing of motion contrast data, there may be room for improvement in various aspects.

For example, the states of blood vessels are visualized by motion contrast data; however, it is not easy to grasp the states of blood vessels only by observing motion contrast data.

The present invention was made in view of at least one of the problems of the technology according to the related art, and a technological object of the present invention is to provide an ophthalmic analysis device and an ophthalmic analysis program capable of suitably performing blood vessel analysis using OCT motion contrast data.

In order to achieve the above-described object, the present invention is characterized by having the following configurations.

An ophthalmic analysis device for analyzing OCT motion contrast data including blood vessel information of a subject eye acquired by an ophthalmic OCT, comprising:

a processor; and memory storing computer readable program, when executed by the processor, causing, the ophthalmic analysis device to execute;

an analysis process of analyzing the OCT motion contrast data to acquire a measurement result related to a capillary area of the subject eye, wherein the analysis process executes an alleviating process for alleviating the influence of great blood vessels having blood vessel diameters larger than those of capillaries on the measurement result to acquire the measurement result related to the capillary area.

DESCRIPTION OF ILLUSTRATIVE EMBODIMENTS

Hereinafter, an ophthalmic analysis device of an embodiment will be described with reference to the accompanying drawings. Also, hereinafter, as an example of the ophthalmic analysis device, an OCT motion contrast data analysis device will be described. An OCT motion contrast data analysis device (hereinafter, referred to as the OCT analysis device) 1 shown in FIG. 1 performs a process of analyzing motion contrast data acquired by an OCT device 10. OCT motion contrast data includes, for example, blood vessel information of a subject eye.

The OCT analysis device 1 includes, for example, a control unit 70. The control unit 70 is implemented, for example, by a general central processing unit (CPU) 71, a ROM 72, a RAM 73, and so on. In the ROM 72, for example, an analysis processing program for processing motion contrast data, a program for controlling operations of the OCT device 10, thereby obtaining motion contrast data, initial values, and so on are stored. The RAM 73 is, for example, for temporarily storing a variety of information.

Figure 1:
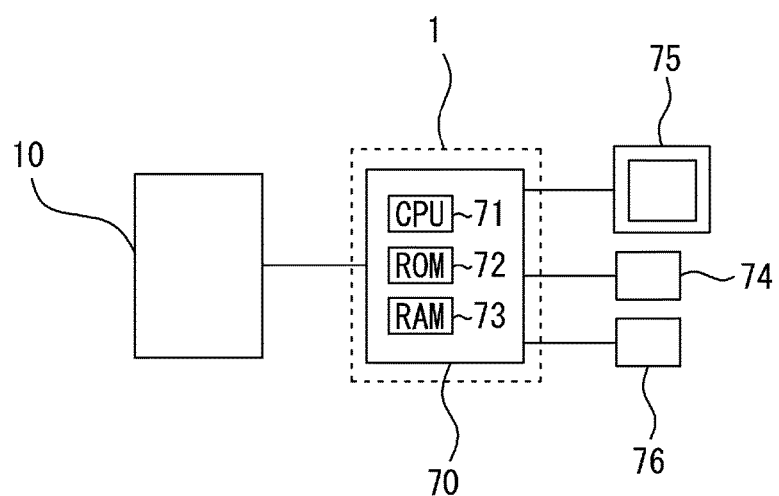
FIG. 1 is a block diagram illustrating the outline of an embodiment.

As shown in FIG. 1, the control unit 70 is electrically connected, for example, to a storage unit (for example, a non-volatile memory) 74, an operation unit 76, a display unit 75, and so on. The storage unit 74 is, for example, a non-transitory storage medium capable of retaining storage contents even if supply of power is interrupted. For example, a hard disk drive, a flash ROM, an attachable/detachable USB memory, and the like can be used as the storage unit 74.

To the operation unit 76, various operation instructions of an examiner are input. The operation unit 76 outputs signals based on the input operation instructions to the CPU 71. As the operation unit 76, for example, at least one user interface of a mouse, a joy stick, a keyboard, a touch panel, and the like may be used.

The display unit 75 may be a display mounted on the main body of the device 1, or may be a display connected to the main body. For example, a display of a personal computer (hereinafter, referred to as a "PC") may be used. The display unit 75 displays, for example, OCT data acquired by the OCT device 10, motion contrast data, and so on.

Also, the OCT analysis device 1 of the present embodiment is connected, for example, to the OCT device 10. Also, the OCT analysis device 1 may be configured integrally with the OCT device 10 inside a single case, or may be configured separately from the OCT device. The control unit 70 may acquire motion contrast data from the connected OCT device 10. The control unit 70 may acquire motion contrast data acquired by the OCT device 10, through a storage medium.

<OCT Device>

Figure 2:
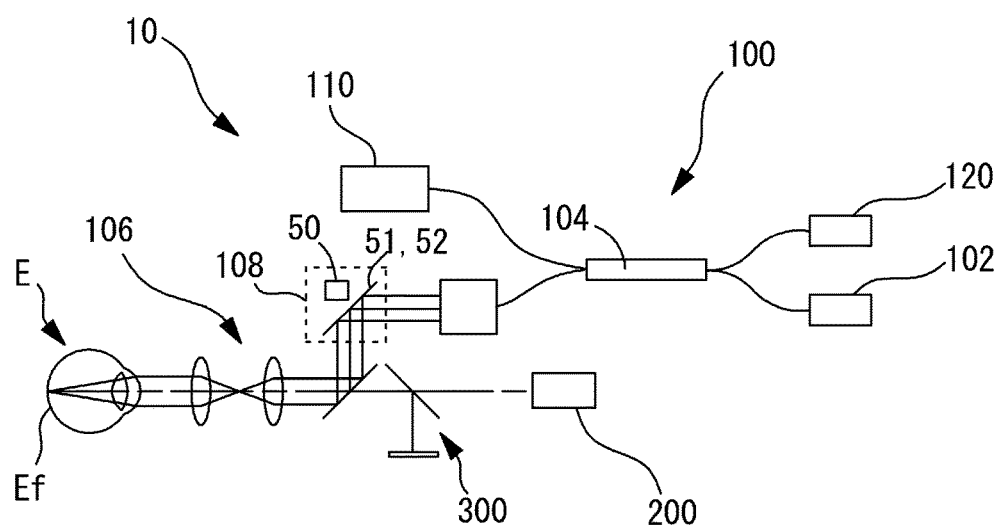
FIG. 2 is a view illustrating an example of an optical system of an OCT device.

Hereinafter, an outline of the OCT device 10 will be described on the basis of FIG. 2. For example, the OCT device 10 irradiates a subject eye E with measurement light, and acquires an OCT signal acquired on the basis of the reflected light of the measurement light and reference light. The OCT device 10 mainly includes, for example, an OCT optical system 100.

<OCT Optical System>

The OCT optical system 100 irradiates the subject eye E with measurement light, and detects an interference signal between the reflected light of the measurement light and the reference light. The OCT optical system 100 mainly includes, for example, a measurement light source 102, a coupler (a light splitter) 104, a measuring optical system 106, a reference optical system 110, a detector 120, and so on. Also, with respect to a detailed configuration of the OCT optical system, for example, Japanese Patent Application Laid-Open No. 2015-131107 can be referred to.

The OCT optical system 100 is a so-called optical coherence tomography (OCT) optical system. The OCT optical system 100 splits light emitted from the measurement light source 102 into measurement light (sample light) and reference light by the coupler 104. The measurement light is guided to the measuring optical system 106, and the reference light is guided to the reference optical system 110. The measurement light is guided to a fundus Ef of the subject eye E through the measuring optical system 106. Thereafter, interference light obtained by synthesizing the measurement light reflected by the subject eye E and the reference light is guided to the detector 120.

The measuring optical system 106 includes, for example, a scanning unit (for example, an optical scanner) 108. The scanning unit 108 may be provided, for example, for scanning the fundus in X and Y directions (a transverse direction) with measurement light. For example, the CPU 71 controls an operation of the scanning unit 108 on the basis of set scan position information, and acquires an OCT signal on the basis of a light reception signal detected by the detector 120. The reference optical system 110 generates the reference light to be synthesized with the reflected light of the measurement light from the fundus Ef. The reference optical system 110 may be a Michelson type, or may be a Mach-Zehnder type.

The detector 120 detects the interference state of the measurement light and the reference light. In a case of Fourier domain OCT, the spectral intensity of the interference light is detected by the detector 120, and a depth profile (an A-scan signal) of a predetermined range is acquired by performing Fourier transform on spectral intensity data.

Also, as the OCT device 10, for example, a spectral-domain OCT (SD-OCT) device, a swept-source OCT (SS-OCT) device, a time-domain OCT (TD-OCT) device, and the like may be used.

<Optical System for Acquiring Front Image>

An optical system 200 for acquiring a front image acquires a front image of the fundus Ef of the subject eye E, for example, by imaging the fundus Ef from the front direction (for example, the optical axis direction of the measurement light). The optical system 200 for acquiring a front image may have the device configuration of a scanning laser ophthalmoscope (SLO) (see Japanese Patent Application Laid-Open No. 2015-66242 for instance), or may have the configuration of a so-called fundus camera type (see Japanese Patent Application Laid-Open No. 2011-10944 for instance). Also, as the optical system 200 for acquiring a front image, the OCT optical system 100 may be used, and a front image may be acquired on the basis of a detection signal from the detector 120.

<Fixation Target Projecting Unit>

A fixation target projecting unit 300 has an optical system for leading the gaze direction of the eye E. The projecting unit 300 has a fixation target to be present for the eye E, and can lead the eye E. For example, the fixation target projecting unit 300 has a visible light source for emitting visible light, and two-dimensionally changes the presentation position of the fixation target. According to this, the gaze direction changes, and as a result, an OCT data acquisition portion changes.

<Acquisition of Motion Contrast Data>

Figure 3A:
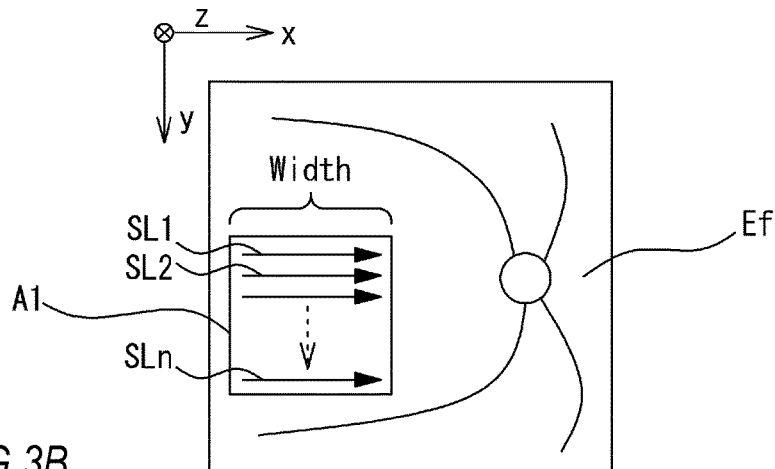
FIGS. 3A to 3C are views for explaining acquiring of motion contrast data.

The OCT analysis device 1 of the present embodiment may acquire motion contrast data, for example, by processing OCT data detected by the OCT device 10. The CPU 71 controls driving of the scanning unit 108 such that the scanning unit scans an area A1 on the fundus Ef with the measurement light. Also, in FIG. 3A, the direction of a z axis is the optical axis direction of the measurement light. The direction of an x axis is perpendicular to the z axis, and is the left-right direction of an examinee. The direction of a y axis is perpendicular to the z axis, and is the vertical direction of the examinee.

For example, the CPU 71 controls the scanning unit such that the scanning unit scans the area A1 in the x-axis direction along scan lines SL1, SL2, . . . , and SLn with the measurement light. Also, scanning in a direction (for example, the x direction) intersecting with the optical axis direction of the measurement light with the measurement light will be referred to as "B-scanning". Further, two-dimensional OCT data which is obtained by performing B-scanning once will be described as two-dimensional OCT data of one frame. The CPU 71 may obtain an A-scan signal of the z direction at each scan position, for example, by performing two-dimensional scanning in the x and y directions with the measurement light.

The CPU 71 may acquire motion contrast data on the basis of OCT data. Motion contrast data may be information representing changes of the blood flow and retinal tissue of the subject eye and so on. In a case of acquiring motion contrast data, the CPU 71 acquires at least two OCT data items on the same position of the subject eye, at different times. For example, on each scan line, the CPU 71 acquires a plurality of OCT data items at different times by performing B-scanning a plurality of times at different times.

Figure 3B:
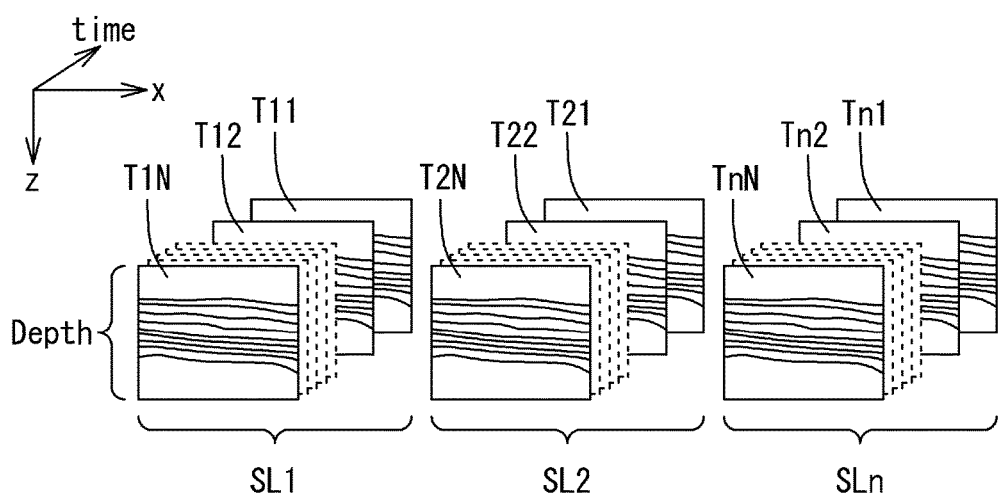
Figure 3C:
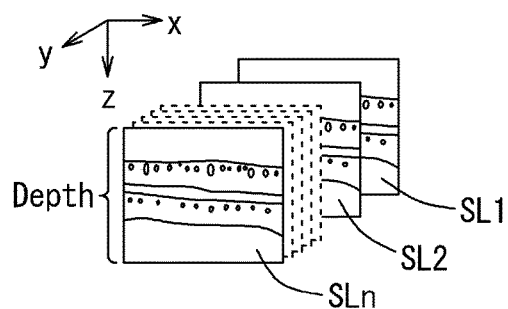

For example, FIG. 3B shows OCT signals which are acquired by performing B-scanning along each of the scan lines SL1, SL2, . . . , and SLn, a plurality of times, at different times. For example, FIG. 3B shows a case of performing scanning along the scan line SL1 at times T11, T12, . . . , and T1N, and performing scanning along the scan line SL2 at times T21, T22, . . . , and T2N, and performing scanning along the scan line SLn at times Tn1, Tn2, . . . , and TnN. For example, the CPU 71 acquires a plurality of OCT data items along each scan line at different times, and stores those OCT data items in the storage unit 74.

If acquiring a plurality of OCT data items on the same position at different times as described above, the CPU 71 processes the OCT data items, thereby acquiring motion contrast data. Examples of an OCT data calculation method for acquiring motion contrast data include a method of calculating the intensity differences or amplitude differences of the plurality of OCT data items, a method of calculating the variance or standard deviation of the intensities or amplitudes of the plurality of OCT data items (speckle variance), a method of calculating the phase differences or variance of the plurality of the plurality of OCT data items, a method of calculating the vector differences of the plurality of OCT data items, and a method of multiplying the phase differences and vector differences of the plurality of OCT data items. Also, as one of the calculation methods, for example, Japanese Patent Application Laid-Open No. 2015-131107 can be referred to.

The CPU 71 may acquire three-dimensional motion contrast data of the subject eye E by arranging motion contrast data items acquired along the different scan lines. Also, as described above, as motion contrast data, phase differences, intensity differences, vector differences, or the like may be acquired.

<Process of Analyzing Motion Contrast Data>

An example of a process of analyzing the motion contrast data acquired as described above will be described below.

The CPU 71 may set an analysis area with respect to the motion contrast data, and acquire at least one analysis result by performing an analyzing process on the set analysis area. In this case, the CPU 71 may set an analysis area of the motion contrast data with reference to position information of an analysis chart on second image data which is image data different from the motion contrast data.

Hereinafter, as an example of the analysis result, a case of extracting a vascular area of the subject eye by performing an analyzing process on the motion contrast data will be described. In this case, a blood vessel analysis area may be set as an analysis area of the motion contrast data, and an analyzing process for extracting a vascular area from at least the blood vessel analysis area may be performed.

Figure 4:
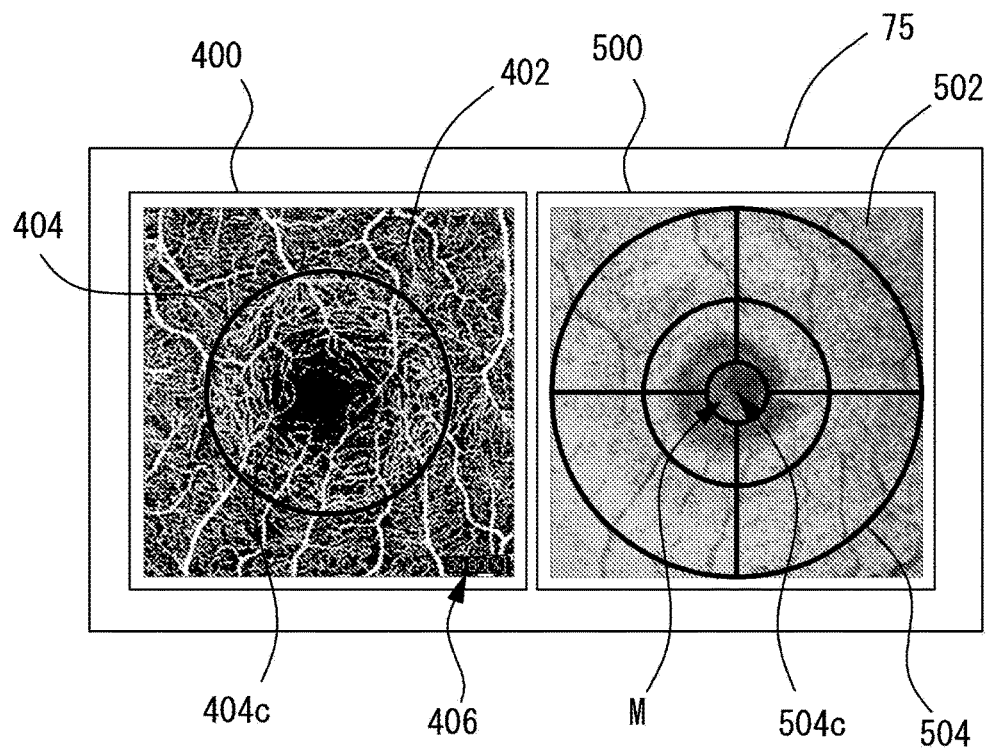
FIG. 4 is a view illustrating an example of a display screen.

FIG. 4 is a view illustrating an example of an analysis screen for extracting a vascular area. For example, the CPU 71 may display a motion contrast display area (hereinafter, referred to as the MC display area) 400 and a second image display area 500, in the analysis screen displayed on a display screen of the display unit 75. In this case, the MC display area 400 and the second image display area 500 may be displayed at the same time, or may be displayed at different timings.

The MC display area 400 is an area for displaying motion contrast data (hereinafter, referred to as MC data) 402, and as the MC data 402, for example, as shown in FIG. 4, front MC data (also referred to as en-face MC data) may be displayed. The front MC data may be acquired, for example, by extracting three-dimensional MC data on at least a partial area in a depth direction (see Japanese Patent Application Laid-Open No. 2015-121574 for instance). For example, the front MC data may be generated by the integrated value or maximum value of the MC data in the depth direction. Obviously, as the MC data 402, one-dimensional MC data, two-dimensional MC data, or three-dimensional MC data may be displayed.

The CPU 71 may create a display (for example, a graphic 404) representing the blood vessel analysis area of the MC data 402, on the MC data 402. The display representing the blood vessel analysis area may be a frame display representing the periphery of the blood vessel analysis area like the graphic 404 of FIG. 4, or may be a display representing the blood vessel analysis area and the other area in different colors.

The second image display area 500 may be an area for displaying second image data 502 which is image data different from the MC data 402. In the second image display area, for example, at least one of a front image and an analysis map may be displayed. As the second image data 502, image data including at least some data which is the same as those of the MC data 402 with respect to the acquisition area is used. For example, in a case where the MC data 402 is data having a macula portion as the center, the second image data 502 on the macula is displayed, and in a case where the MC data 402 is data having an optic disc portion as the center, the second image data 502 on the optic disc may be displayed.

The analysis map may be, for example, a map representing a two-dimensional distribution of measurement results of the fundus. In this case, the analysis map may be, for example, a color map representing measurement values in different colors. Examples of the analysis map include a thickness map representing layer thickness, a comparison map representing the results of comparison between the layer thickness of the subject eye and the layer thicknesses of normal eyes stored in a normal eye database, a deviation map representing the standard deviation of deviations between the layer thickness of the subject eye and the layer thicknesses of the normal eyes stored in the normal eye database, and an examination date comparison thickness difference map representing the thickness differences between examination dates. Also, in a case of obtaining the thicknesses of layers, for example, the OCT data are divided in units of a layer, for example, by performing image processing (for example, a segmentation process) on the OCT data, and the thickness of each layer is measured on the basis of the intervals between layer boundaries. Obviously, the analysis map is not limited to layer thicknesses, and may be, for example, a map representing the curvature distribution of the fundus.

The front image may be, for example, a front image acquired by the optical system 200 for acquiring a front image, or may be front OCT data (also referred to as en-face OCT data) which is generated from three-dimensional OCT data. The three-dimensional OCT data may be three-dimensional OCT data to be the base of three-dimensional motion contrast data. The analysis map may be, for example, a color map two-dimensionally representing the result of analysis of the subject eye (such as the thickness and curvature of the fundus layer). FIG. 4 shows an image obtained by superimposing the analysis map on the front image, as the second image data 502.

<Analysis Chart>

The CPU 71 may display an analysis chart 504 on the second image data 502. In this case, the second image data 502 may be associated in advance with a measurement result (for example, measurement data of the analysis map) based on the result of analysis of the three-dimensional OCT data (registration), and a measurement result corresponding to an area where the analysis chart 504 has been set is output. In this case, the second image data 502 may be associated with three-dimensional OCT data, and an analyzing process may be performed on the area where the analysis chart has been set, and on the basis of the analysis result, a measurement result may be output. In this case, it is preferable that the three-dimensional OCT data be three-dimensional OCT data based on the MC data. The reason is that positional association of the MC data and the second image data (registration) is easy and accurate.

For example, the analysis chart 504 may be an analysis chart for measuring a basic statistic of measured results of preset sections, and basic statistics of the sections may be measured. The number of sections which form the analysis chart 504 may be one, or may be two or more. In a case where the analysis chart consists of a plurality of sections, a basic statistic may be measured in each section. As a basic statistic may be a representative value (such as an average value, a median, a mode, a maximum value, or a minimum value), the degree of scatter (dispersion, standard deviation, or the coefficient of variation), or the like.

For example, the analysis chart 504 may be a chart for obtaining the average of each area with respect to a two-dimensional distribution of the layer thickness of the fundus. Also, the analysis chart 504 may have a numerical-value display area for numerically displaying the layer thickness of a predetermined area. Instead of numerical-value display, color coding according to measurement results may be performed in units of a section. Layer thickness data may be the sum of individual layers, or may be the thickness of a certain layer (for example, an optic nerve fiber layer).

In a case where the analysis charts 504 is arbitrarily selectable, and a thickness map is a macula map, for example, the examiner can select one of a GCHART (specifically, a chart which has been divided into three sections in a radial direction and has been divided in a vertical direction and a horizontal direction passing the center of the chart), an S/I chart, and an ETDRS chart, as the analysis chart 504. Meanwhile, in a case where the thickness map is an optic-disc map, for example, it is possible to select one of a chart consisting of one section, a chart consisting of an upper section and a lower section (two sections), a TSNIT (Temporal Superior Nasal Inferior Temporal) chart (four sections), and a ClockHour chart (twelve sections), as the analysis chart.

The CPU 71 may change the display position of the analysis chart 504 on the second image data 502, in response to reception of an operation signal from the operation unit 76. In this case, the analysis area of the second image data 502 which is defined by the analysis chart 504 is changed. The CPU 71 may obtain the result of analysis of the analysis area changed according to the change in the display position of the analysis chart 504. Also, a portion of the analysis chart may protrude from the second image data 502.

For example, the examiner may set the center 504c of the analysis chart at a reference portion of the fundus (for example, the center of the central fovea (see a reference symbol "M" of FIG. 4), the center of the optic disc, or an abnormal portion) by moving the analysis chart 504 by the operation unit 76. In this way, for example, the reference portion of the fundus is set as the center, and measurement results using the analysis chart 504 are obtained. For example, the average layer thickness in the whole of the chart having the reference portion as the center, the layer thickness of the reference portion, the average layer thickness (for example, 1 mm, 2 mm, or 3 mm) in a predetermined area having the reference portion as the center, and the like may be measured. In this way, measurement results having the reference portion of the fundus as the center are obtained. Therefore, the measurement results are clinically useful.

<Movement of Blood Vessel Analysis Area with Movement of Analysis Chart>

For example, the CPU 71 may perform extraction of a vascular area on the MC data, using the position information of the analysis chart 504. More specifically, the CPU 71 may move the position of the blood vessel analysis area on the MC data with movement of the analysis chart 504. In this case, the CPU 71 may move the display representing the blood vessel analysis area (for example, the graphic 404) on the MC data 402. In short, the position of the blood vessel analysis area changes with movement of the analysis area which is defined by the analysis chart 504.

As a result of movement of the blood vessel analysis area, the blood vessel area on the MC data changes. Then, according to the change of the blood vessel analysis area, the CPU 71 may obtain the result of analysis of the changed blood vessel analysis area (the blood vessel analyzing method will be described below).

In a case of moving the blood vessel analysis area with movement of the analysis chart, the CPU 71 may move the blood vessel analysis area such that the center 504c of the analysis chart 504 on the second image data 502 and the center 404c of the blood vessel analysis area on the MC data 402 are disposed at the same position in terms of analysis. In other words, the CPU 71 may set the center of the analysis area on the MC data 402 at a position of the second image data 502 corresponding to the center position of the analysis chart 504. In this case, it is preferable that the second image data 502 and the MC data 402 be positionally associated with each other (registration).

Here, for example, in a case where the examiner sets the center 504c of the analysis chart 504 at the reference portion of the fundus (such as the center of the central fovea, the center of the optic disc, or an abnormal portion), the center of the blood vessel analysis area is automatically set at the reference portion of the fundus. Therefore, it is possible to make the analysis reference position of analysis using the analysis chart 504 identical to that of analysis on the MC data 402, without changing the analysis area on the MC data 402 again.

<Setting of Blood Vessel Analysis Area>

The examiner may be arbitrarily set a blood vessel analysis area. For example, the CPU 71 may change the position of the blood vessel analysis area on the MC data, in response to reception of an operation signal from the operation unit 76. In this case, the CPU may change the position of the display representing the blood vessel analysis area. According to the change of the blood vessel analysis area, the CPU 71 may obtain the result of analysis of the changed blood vessel analysis area. In this case, the CPU 71 may move the position of the analysis chart 504 on the second image data 502 with movement of the blood vessel analysis area. As a result, it is possible to save the effort for adjusting the position of the analysis chart 504.

Also, in a case of performing analysis of a plurality of motion contrast data items, a method of setting the position of the blood vessel analysis area on a second motion contrast data item according to change in the position of the blood vessel analysis area on a first motion contrast data item may be used. For example, this method can be applied to analysis of a plurality of different motion contrast data items obtained in the depth direction of the fundus. Also, the CPU 71 may use a first data area set on the first motion contrast data item to remove artifacts from a second data area on the second motion contrast data item positionally corresponding to the first data area (for example, by subtracting the luminance of each pixel of the first data area from the luminance of each pixel of the second data area).

The range (size) of the blood vessel analysis area may be settable by the examiner. The range of the blood vessel analysis area may also be settable according to the area of the fundus for acquiring the MC data 402. As this acquisition area, acquisition areas different in the position in the direction of the front of the fundus may be settable. For example, with respect to the macula portion and the optic disc portion, ranges may be set, respectively.

As setting according to acquisition areas, it may be possible to perform setting according to acquisition areas different in the position in the depth direction of the fundus. For example, with respect to different blood vessel layers, ranges may be set, respectively. Obviously, the present invention is not limited to blood vessel layers, and with respect to different retina layers (or choroid layers), ranges may be set, respectively. This setting makes it possible to perform blood vessel analysis according to acquisition areas on the fundus. In a case where a plurality of front MC data items is generated for each blood vessel layer, it may be possible to set the ranges of blood vessel analysis areas on the front MC data items of individual blood vessel layers, in advance, respectively. This setting makes it possible to perform blood vessel analysis according to each blood vessel layer.

Figure 5:
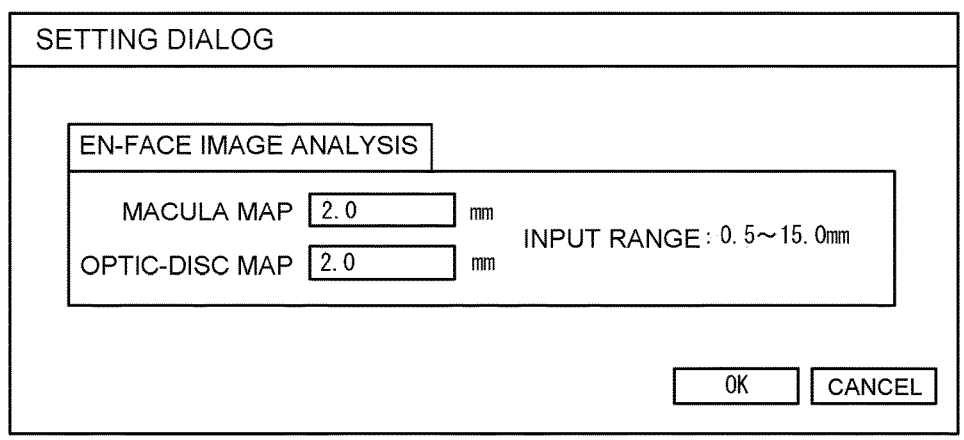
FIG. 5 is a view illustrating an example of a setting screen.

FIG. 5 shows an example of a setting screen, and the macula map represents motion contrast data having the macula as the center, and the optic-disc map represents motion contrast data having the optic disc as the center, and ranges (for example, diameters) are set in units of a map. Also, in a case of setting ranges, for example, the CPU 71 may change the range (size) of the graphic 404 in response to reception of an operation signal from the optical sensor 72. Also, the range of the blood vessel analysis area may be the same range as the analysis chart 504. Also, on the basis of the range of the analysis chart 504, the range of the blood vessel analysis area may be set.

Also, as described above, as change parameters of the blood vessel area, the position and range (size) of the blood vessel analysis area are settable; however, the present invention is not limited thereto. For example, the shape of the blood vessel analysis area may be settable (for example, a circle, an ellipse, a rectangle, or the like). In this case, the shape of the blood vessel analysis area may be settable according to the area of the fundus for acquiring the MC data 402.

The blood vessel analysis area may be an area consisting of a plurality of sections, and blood vessel analysis may be performed on each section. A plurality of blood vessel analysis areas different in either the arrangement positions or ranges (sizes) of the individual sections may be selectable.

In this case, a division parameter of the blood vessel analysis area may be settable according to the area of the fundus for acquiring the MC data 402. For example, for superficial capillary plexus, the entire chart (one section) may be set, and for intermediate capillary plexuses, the S/I chart (two sections of the upper and lower sections) may be set. In this case, the arrangement position and range of each section of the blood vessel analysis area may be set to be the same as the arrangement position and range of each section of the analysis chart 504. In this case, it is possible to evaluate the analysis result of each section of the analysis chart 504 and the analysis result of each section of the blood vessel analysis area in association with each other. Therefore, it is possible to confirm the association between the blood vessel analysis result of the fundus and the morphology analysis result (for example, the layer thickness) of the fundus, in units of a section.

<Blood Vessel Extracting Process and Blood Vessel Measurement>

The CPU 71 may display the measurement result of the set blood vessel analysis area on the display unit 75 by analyzing the blood vessel analysis area set on the MC data 402 as described above. In this case, it is possible to smoothly perform measurement in the analysis chart and measurement on the MC data 402. Also, the analysis result may be displayed, for example, as a numerical value 406 on the MC display area 400.

For example, the CPU 71 performs a process of determining a vascular area and an avascular area by performing analysis using image processing on the area set as the blood vessel analysis area on the MC data. By the determining process, a vascular area is extracted. In this case, by the determining process, an avascular area may be extracted.

The determining process may be a threshold process, and it may be possible to determine a pixel satisfying a threshold, as a vascular area, and determine a pixel which does not satisfying the threshold, as an avascular area. The threshold may be arbitrarily settable by the examiner, or may be determined as a fixed value in advance. Also, the threshold may be set through an image analyzing process on the MC data 402.

For example, the CPU 71 may be configured to perform measurement on the vascular area on the basis of the result of the determining process. On the basis of the vascular area extracted by the determining process, the CPU 71 may measure the vascular area. The measurement result may be, for example, blood vessel density or blood vessel area. As the density of the vascular area, blood vessel area (blood vessel quantity) per unit area can be obtained by obtaining the ratio of the vascular area in the entire blood vessel analysis area. However, the measurement result is not limited thereto, and may be, for example, the total quality of blood vessels, the degree of tortuosity of blood vessels, the regularity of blood vessels, or the like. Also, in a case where the blood vessel analysis area consists of a plurality of sections, the CPU 71 may obtain the measurement result ratio or difference between the individual sections. In this case, for example, it is possible to obtain the symmetry of blood vessels, or the like.

<Determination of Capillaries>

Hereinafter, a process of acquiring a result of measurement on a capillary area will be described. In a case of performing measurement on a capillary area, the CPU 71 may perform the process of determining a vascular area and an avascular area, and then perform analysis using image processing on an area determined as the vascular area, thereby performing a process of determining great blood vessels and capillaries. By this determining process, a capillary area is extracted.

The determining process may be, for example, a determining process using a determining process using blood vessel diameters, and it may be possible to determine a blood vessel having a blood vessel diameter smaller than a threshold, as the capillary area, and determine a blood vessel having a blood vessel diameter exceeding the threshold, as a great-blood-vessel area. This uses that, with respect to blood vessels, capillaries are thin and great blood vessels are thick. It is possible to use blood vessel diameters to accurately distinguish between capillaries having small blood vessel diameters and great blood vessels having large blood vessel diameters. Also, in a case of obtaining blood vessel diameters, the CPU 71 may measure the diameter of each blood vessel included in the vascular area by image processing. For example, the CPU 71 may perform thinning on the vascular area detected from the MC data, and measure the original blood vessel diameter from thinned lines. However, the method of measuring blood vessel diameters is not limited thereto, and, for example, the distance between walls of each blood vessel (for example, the inter-intima distance) may be measured.

The determining process may be, for example, a determining process using the number of branches of each blood vessel, and it may be possible to determine a blood vessel having branches more than a threshold as the capillary area, and determine a blood vessel having branches less than the threshold as the great-blood-vessel area. This uses that, with respect to the numbers of branches of blood vessels, a capillary has a large number of branches and a great blood vessel has a small number of branches. It is possible to use the numbers of branches to accurately distinguish between capillaries which are located at the relatively distal end and great blood vessels which are located at the relatively proximal end. In this case, the number of branches of each blood vessel from the optic disc portion may be a reference, or the number of branches from a largish blood vessel of great blood vessels may be a reference. In a case of obtaining the numbers of branches of blood vessels, the CPU 71 may be extract the branch points of the blood vessels by image processing, and measure the number of branch points of each blood vessel. Also, the determining process may be performed using combinations of blood vessel diameters and the numbers of branches of blood vessels. In this case, the determination accuracy is improved.

Also, in the above description, as the process of determining great blood vessels and capillaries, the cases using blood vessel diameters and/or the numbers of branches have been described as examples; however, the present invention is not limited thereto. For example, the determining process may be a determining process using differences in blood flow rate between blood vessels. More specifically, it is possible to determine a blood vessel having a blood flow rate lower than a threshold, as the capillary area, and determine a blood vessel having a blood flow rate exceeding the threshold, as the great-blood-vessel area. This uses that capillaries have low blood flow rates and great blood vessels have high blood flow rates. Also, blood flow rate may be detected using a difference in luminance between capillaries and great blood vessels in the MC data. In this case, capillaries are imaged relatively bright, and great blood vessels are imaged relatively darkly.

Also, in a case where the determining process uses a threshold for blood vessel diameters, the numbers of branches, or the like, the threshold may be arbitrarily settable by the examiner, or may be determined as a fixed value in advance. In a case of a fixed value, the threshold is changed according to the properties (for example, ages or genders) of examinees. In short, a reference for determining great blood vessels and capillaries may be set by the examiner. Also, the process of determining great blood vessels and capillaries may be performed through operations of the examiner, and determination results may be obtained as the examiner sequentially designates the capillary area on the MC data. Obviously, if the great blood vessel is designated, as a result, the capillary area other than the great blood vessel may be specified.

Figure 6:
FIG. 6 shows examples of results of a determining process.
Figure 6:
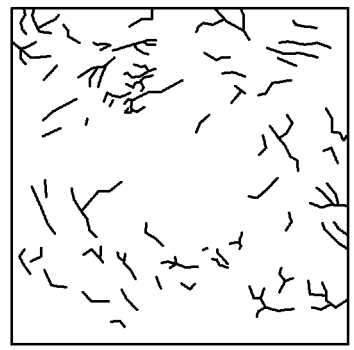
Figure 6:
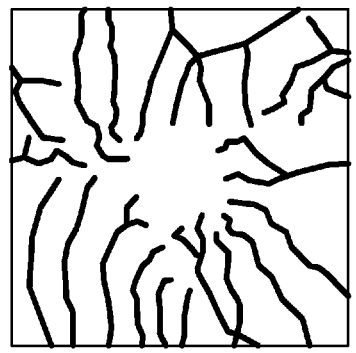

FIG. 6 shows an example of a result of the determining process, and as shown in FIG. 6, from MC data (the top view) on all blood vessels, MC data (the middle view) on capillaries and MC data (the bottom view) on great blood vessels may be determined. Also, in the above-described process, the capillary area may be extracted, and it is not necessarily needed to extract the great-blood-vessel area.

<Measurement of Capillaries Less Likely to be Influenced by Great Blood Vessels>

The CPU 71 may acquire a measurement result of the capillary area by analyzing the MC data. For example, the CPU 71 may acquire a measurement result of the capillary area through an alleviating process for alleviating the influence of great blood vessels having blood vessel diameters larger than those of capillaries on the measurement result. In this case, the CPU 71 may execute the alleviating process for alleviating the influence of great blood vessels having blood vessel diameters larger than those of capillaries on the measurement result, and acquire the measurement result of the capillary area.

The alleviating process may be, for example, an alleviating process specified for the vascular area smaller than a predetermined blood vessel diameter. Also, the CPU 71 may perform a process of specifying the capillary area from the MC data, and may acquire a measurement result of the capillary area on the basis of the specified capillary area. Also, the CPU 71 may determine the great-blood-vessel area and the capillary area in the vascular area, and perform a measuring process on an area determined as the capillary area. In other words, the determination result may be used. Also, the CPU may specify an area surrounded by the vascular area, and acquire measurement results of capillaries on the basis of the specified area. Also, the CPU may specify capillaries by the difference between the MC data and a fundus front image. As the fundus front image, a front image acquired by a fundus camera or an SLO may be used.

Hereinafter, an example of the alleviating process will be described. For example, the CPU 71 may perform measurement on the capillary area on the basis of the result of the determining process. In this case, on the basis of the capillary area determined by the determining process, the CPU 71 may measure the vascular area which is the capillary area. The measurement result may be, for example, the blood vessel density of capillaries or the blood vessel area of capillaries. As the blood vessel density of capillaries, the capillary area (quantity) per unit area can be obtained, for example, by obtaining the ratio of the capillary area in the entire blood vessel analysis area. However, the measurement result is not limited thereto, and may be, for example, the total quantity of capillaries, the degree of tortuosity of capillaries, the regularity of capillaries, or the like. Also, in a case where the blood vessel analysis area consists of a plurality of sections, the CPU 71 may obtain the measurement result ratio or difference between the individual sections. In this case, for example, it is possible to obtain the symmetry of capillaries, or the like.

According to the above-described measuring process, for example, since measurement specified for capillaries is performed, the influence of great blood vessels is alleviated, and it is possible to more accurately perform measurement on capillaries. Therefore, for example, it is possible to more accurately evaluate eye diseases related to capillaries. Meanwhile, in a case of measurement including great blood vessels, great blood vessels have a certain ratio in the blood vessel analysis area, and may bury or change measurement blood vessels related to capillaries.

Also, in the above description, great blood vessels and capillaries are determined, and a measurement result of an area determined as the capillary area is acquired. However, the present invention is not limited thereto. The CPU 71 may perform a measuring process including great blood vessels and capillaries by a calculation process constructed to reduce the ratio of the great-blood-vessel area by weighting calculation. In this case, the CPU 71 may perform image processing for performing thinning on an area determined as the great-blood-vessel area such that it becomes as thin as capillaries, and then perform a measuring process including the great-blood-vessel area and the capillary area. Even by the above-described process, a measurement result less influenced by great blood vessels is obtained. Also, in the above description, the example in which measurement is performed on the capillary area has been shown. However, the present invention is not limited thereto, and measurement on the great-blood-vessel area extracted through the determining process may be performed.

<Two-Dimensional Measurement on Capillaries and Acquisition of Blood Vessel Analysis Map>

The CPU 71 may acquire a two-dimensional or three-dimensional measurement result of the capillary area. Also, the CPU 71 may output a color map color-coded according to measurement results of individual positions of the capillary area.

For example, the CPU 71 may perform a measuring process on two-dimensional positions of the capillary area. In this case, for example, the measuring process may be performed in units of one pixel or a plurality of pixels forming the capillary area. Also, a measurement range may be, for example, a set range set at a portion of the MC data, or may be the whole of the MC data. The set range which is set at a portion of the MC data may be set so as to have a reference portion of the fundus (for example, the central fovea, the center of the optic disc, or an abnormal portion) as the center. The set range may be a certain range set in advance, or may be a range arbitrarily set by the examiner. Also, the shape of the set range may be arbitrarily changed.

Figure 7:
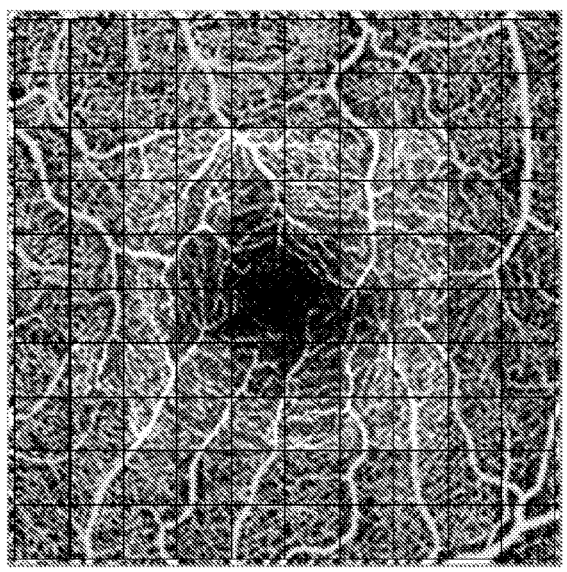
FIG. 7 shows an example of a case of dividing a capillary area into a plurality of sections and performing measurement.

For example, the CPU 71 may divide the capillary area into a plurality of sections, and perform the measuring process on each section (see FIG. 7 for instance). In this case, for example, the CPU 71 may acquire a measurement result of each micro area. More specifically, the CPU may acquire a measurement result of each section by dividing two-dimensional 256-by-256 MC data in units of two-dimensional 8-by-8 MC data. Also, the CPU 71 may acquire a measurement result of each relatively wide area (for example, each two-dimensional area). More specifically, the CPU may acquire a measurement result of each section by longitudinally and laterally dividing the two-dimensional 256-by-256 MC data (for example, into 3-by-3 sections or 4-by-4 sections). Also, the process of measuring capillaries does not necessarily need to acquire quantitative measurement values, and may be a method of acquiring measurement results in a stepwise fashion (for example, grade classification).

The CPU 71 may acquire a blood vessel analysis map on the basis of the measurement result of the capillary area (see FIG. 7 for instance). The blood vessel analysis map may be displayed on the screen of the display unit 75.

The blood vessel analysis map may be, for example, a map representing a two-dimensional distribution of the measurement result of the capillary area. The blood vessel analyzing method may be, for example, a color map color-coded according to the measurement values of two-dimensional positions. In this case, the CPU 71 may determine display colors according to the measurement values of the two-dimensional positions, and display the positions in the determined display colors. Also, the display colors may be display colors set in advance according to the magnitudes of the measurement results, or may be arbitrarily set according to the measurement results by the examiner. More specifically, the blood vessel analysis map may be, for example, a color map color-coded according to the measurement results of individual sections. The CPU 71 may determine display colors according to the measurement results of the individual sections, and display the individual sections in the determined display colors.

Also, in the blood vessel analysis map, with respect to great blood vessels, color cording display may not be performed. Also, the measurement results of the great blood vessels may be displayed in a color different from a color according to the measurement results of capillaries. In this case, since the capillaries and the great blood vessels are distinguished, the examiner can accurately evaluate the capillaries. Also, the blood vessel analysis map may be displayed on the MC data, and in this case, on the great blood vessels of the MC data, the color of the map may not be displayed, or may be displayed in a color distinguishable from the capillary area.

Also, the type of the blood vessel analysis map may be, for example, at least one of a basic map, a comparison map, a difference map, and an examination date difference map. More specifically, the basic map may be a basic map two-dimensionally representing the magnitudes of the measurement values of the subject eye related to capillaries (for example, a blood vessel density map). The comparison map may be a comparison map representing a result of comparison between a measurement value of the subject eye related to the capillaries and normal eye data related to capillaries and stored in the normal eye database. The difference map may be a deviation map (a difference map) representing a deviation between a measurement value of the subject eye related to capillaries and the normal eye data related to capillaries and stored in a blood vessel information database. The examination date difference map may be an examination date difference map representing a difference in the measurement value of the subject eye related to capillaries between examination dates.

In a case of acquiring a blood vessel analysis map, for example, the MC data may be divided in units of a layer, and with respect to at least one layer, a blood vessel analysis map may be acquired. In this case, a plurality of blood vessel analysis maps related to different layer areas may be acquired. Also, blood vessel analysis maps of a plurality of layer areas may be acquired. Also, division in units of a layer may be performed by image processing (for example, segmentation) on the MC data, or a result of image processing (for example, segmentation) on the OCT data which is the base of the MC data may be applied to the MC data.

Figure 8:
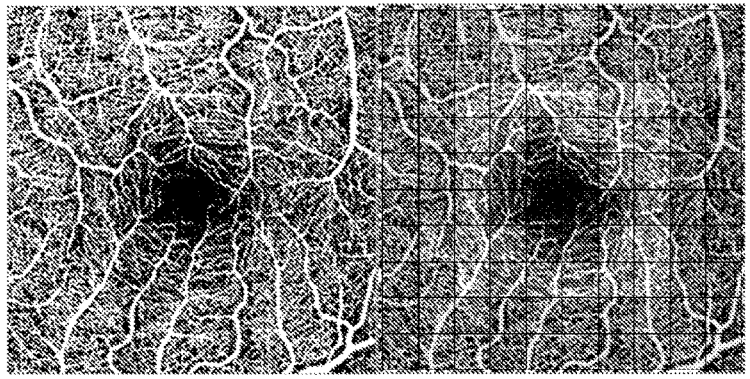
FIG. 8 shows a display example of a blood vessel analysis map and MC data.

Also, in a case of displaying a blood vessel analysis map, for example, the CPU 71 may display the blood vessel analysis map and the MC data (for example, two-dimensional MC data) which is the base of the blood vessel analysis map, on the same screen of the display unit 75 at the same time (see FIG. 8 for instance).

For example, the CPU 71 may display the acquired blood vessel analysis map on the MC data of the subject eye. In this case, it is possible to easily confirm blood vessel loss areas of the MC data. Also, in the case of superimposing the blood vessel analysis map, the CPU 71 may perform display such that areas exceeding a normal range of the normal eye data are highlighted as abnormal areas. For example, the CPU 71 may superimpose the acquired blood vessel analysis map on a front image of the subject eye. A fundus front image may be an infrared front image, a color front image, or a front image based on the OCT data.

Also, the CPU 71 may change the blood vessel analysis map according to measurement portions. In this case, maps to be output may be set according to measurement portions in advance, or may be arbitrarily settable by the examiner.

For example, according to measurement portions, the number of sections of a blood vessel analysis map may be changed. More specifically, for example, with respect to the MC data of the macula portion, the number of sections may be set to be relatively large, and with respect to the MC data of the optic disc portion, the number of sections may be set to be relatively small. This is because there is a possibility that, with respect to the macula portion, a detailed measurement result will be obtained, and with respect to the optic disc portion, a general measurement result will be obtained. Also, according to measurement portions, a depth area of the MC data which is the base of a blood vessel analysis map may be changed. More specifically, for example, with respect to the MC data of the macula portion, a blood vessel analysis map related to front areas (for example, NFL to IPL) of a retina may be set, and with respect to the optic disc portion, a blood vessel analysis map related to the entire area (for example, NFL to RPE) of the retina may be set.

Also, the CPU 71 may perform changing between blood vessel analysis maps according to analysis diseases. In this case, maps to be output may be set according to measurement portions in advance, or may be arbitrarily settable by the examiner.

For example, according to analysis diseases, at least one of the number of sections of a blood vessel analysis map, the arrangement positions of sections, and a depth area of the MC data which is the base of a blood vessel analysis map may be changed. For example, in a case of diabetic retinopathy, in a relatively shallow area (front side) of the retina, ischemia occurs.

Meanwhile, in cases of BRVO (Branch retinal vein occlusion), CRVO (Central retinal vein occlusion), BRAO (Branch retinal artery occlusion), or CRAO (Central retinal artery occlusion), in the entire retina, ischemia occurs. For this reason, a depth area of MC data is changed according to diseases, whereby it is possible to suitably perform evaluation of lesions.

Also, with respect to the number of sections of a blood vessel analysis map, for example, in a case of CRVO, since it is caused by the vicinity of the optic disc, sections may be uniformly set over the entire fundus in the direction of the front (a direction perpendicular to a depth direction). Meanwhile, in a case of BRVO, since it occurs on the supertemporal side, with respect to the supertemporal side, the number of sections may be set to be large, and with respect to the other areas, the number of sections may be set to be small. In short, according to lesions, at least one of the number of sections and the arrangement positions of sections may be changed.

<Examples of Blood Vessel Density Map>

Hereinafter, as an example of the blood vessel density map, a blood vessel density map representing a two-dimensional distribution of blood vessel density related to capillaries will be described (see FIGS. 7 and 9).

A map of FIG. 7 is an example of a color map color-coded according to measurement values (blood vessel densities) of individual sections. For example, the CPU 71 may generate a color map according to measurement values of pre-set sections, and display the generated color map on the display unit 75. By changing display colors according to the measurement values, it is possible to easily grasp loss of the blood vessels.

Further, in a case of displaying a color map in units of a section as described above, at least one of the shape and number of sections may be arbitrarily changed. In this way, density display according to diseases may be performed.

Also, the CPU 71 may compare blood vessel density distribution data stored in the blood vessel information database and blood vessel density distribution data of the subject eye with respect to the same range as that of an acquired blood vessel density map, and display of the comparison result makes it possible for the examinee to easily confirm the blood vessel loss state of the subject eye related to normal eyes. In a case of displaying the comparison result, a difference map of normal eye data and subject eye data is useful. Also, the CPU 71 may display a blood vessel density map based on the normal eye data, and a blood vessel density map based on the subject eye data, as the comparison result, on the display unit 75, at the same time.

Also, the CPU 71 may compare past blood vessel density distribution data of the subject eye stored in the blood vessel information database, and current blood vessel density distribution data of the subject eye, with respect to the same range as that of an acquired blood vessel density map, and display of the comparison result makes it possible for the examinee to easily confirm temporal change in the blood vessel loss state. In a case of displaying the comparison result, a difference map of past subject eye data and current subject eye data is useful. Also, the CPU 71 may display a blood vessel density map based on the past subject eye data, and a blood vessel density map based on the current subject eye data, as the comparison result, on the display unit 75, at the same time.

Figure 9:
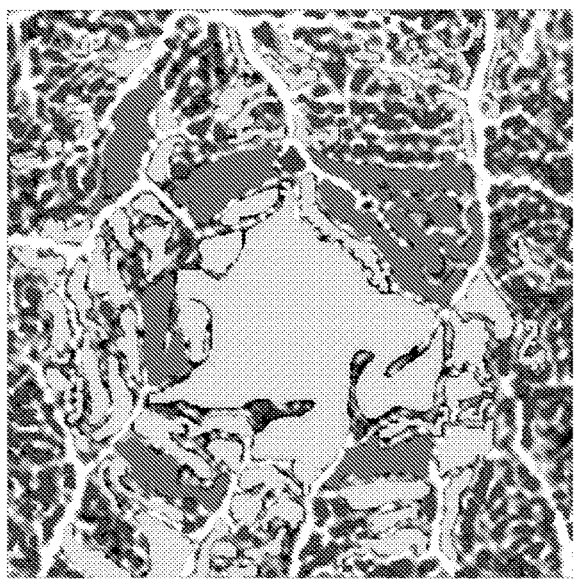
FIG. 9 shows an example of a blood vessel density map.

Also, as a blood vessel analysis map display method, for example, the CPU 71 may obtain a two-dimensional distribution of measurement results related to capillaries as shown in FIG. 9 by specifying an area surrounded by blood vessels on the basis of the vascular area of the MC data.

In this case, the CPU 71 may specify an area surrounded by blood vessels, for example, by determining connectivity of blood vessels by image processing, and determining whether the avascular area is surrounded by blood vessels. In this case, the avascular area does not necessarily need to be surrounded 360 degrees, and if the avascular area is surrounded to a certain extent, it may be determined as an area surrounded by blood vessels.

More specifically, the CPU 71 may calculate the area of the area surrounded by blood vessels. The CPU 71 may also perform color-coded display of each area according to the calculated area. In color coding, at least two colors can be used. For example, as shown in FIG. 9, narrow areas may be displayed in a first color (for example, red), and wide areas may be displayed in a second color (for example, green). As loss of capillaries progresses, the ratio of first color areas decreases, and the ratio of second color areas increases. Therefore, on the basis of color distribution of them, it is possible to easily grasp loss of capillaries. According to this display method, since blood vessels are not counted as area, as a result, the influence of great blood vessels is alleviated, and it is possible to accurately grasp the loss state of capillaries.

Also, in a case of obtaining the loss state of capillaries, in an avascular area, a portion having a distance from the closest blood vessel equal to or greater than a threshold may be displayed in a different color.

Also, in the above description, the blood vessel density maps have been described as examples. However, the present invention is not limited thereto, and it is goes without saying that the above-described display form can be applied to other blood vessel analysis maps.

<Blood Vessel Information Database>

In the storage unit 74, the blood vessel information database may be stored. Data stored in the blood vessel information database may be used, for example, in comparison with an acquired measurement result of the subject eye, and at least one of blood vessel measurement results (such as blood vessel density, blood vessel area, the total quantity of capillaries, the degree of tortuosity of capillaries, and the regularity of capillaries) which are measurement results related to blood vessels can be stored as a database.

The blood vessel information database may be, for example, a normal eye database, and blood vessel measurement results of normal eyes are stored. The normal eye database may be used, for example, in comparison with a measurement result of the subject eye measured actually.

The normal eye database may be generated by integrating blood vessel measurement results of a number of normal eyes, and, for example, statistical measurement results acquired from blood vessel measurement results of a number of normal eyes may be stored. In this case, the normal eye database may be constructed, for example, by acquiring blood vessel measurement results of a number of eyes, and integrating the blood vessel measurement results of the normal eyes. Also, such a normal eye database may be constructed for each of race, gender, and eye properties (for example, the axial length of each eye), and be stored in the storage unit 74.

The blood vessel information database may be, for example, a follow-up database, and past blood vessel measurement results of each subject eye are stored. The follow-up database may be used, for example, in comparison with a newly acquired measurement result of each subject eye, and may be used in comparison between past measurement results acquired at different times. In the follow-up database, for example, measurement results which are acquired for a follow-up duration may be stored together with measurement times (for example, dates and times) may be stored for each examinee.

As such a blood vessel information database, a database less likely to be influenced by great blood vessels is constructed by alleviating the influence of great blood vessels, and then acquiring measurement results, and making a database of them. By using this blood vessel information database, it is possible to more accurately perform analysis of capillaries of each subject eye.

<Blood Vessel Measurement Considering Depth Direction>

In a case of performing blood vessel measurement, the CPU 71 may acquire a measurement result related to the vascular area in a specific depth area by analyzing the MC data. Further, the CPU 71 may correct the measurement result on the basis of the measurement range of the depth area. The vascular area in the specific depth area may a predetermined layer (which may be the whole of a retina layer, or may be the whole of a choroid), or may be data which is a portion of three-dimensional data and from which the depth area has been extracted.

Figure 10:
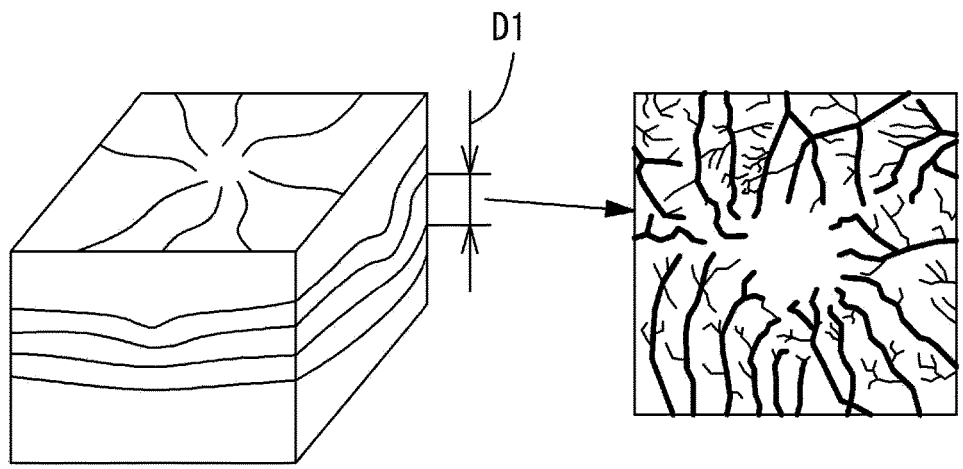
FIG. 10 is a view illustrating an example of a case of performing blood vessel measurement in view of a depth direction.

For example, the CPU 71 may be configured to perform measurement on the vascular area in view of the measurement range in the depth direction. For example, the CPU 71 may correct the measurement result of the vascular area calculated on the basis of the MC data, on the basis of the measurement range in the depth direction. For example, the CPU may correct a two-dimensional measurement result of the vascular area calculated on the basis of front MC data, on the basis of the measurement range in the depth direction. A measurement range in the depth direction may be, for example, the size of a measurement range D1 in the depth direction corresponding to front MC data used in blood vessel measurement as shown in FIG. 10. In this case, the CPU 71 may correct the measurement result of the vascular area calculated on the basis of the front MC data, on the basis of the size of the measurement range D1.

The MC data related to the specific depth area may be OCT front motion contrast data based on three-axis data motion contrast data of the specific depth area, and the CPU 71 may correct a two-dimensional measurement result related to the vascular area of the specific depth area, on the basis of the measurement range of the depth area.

More specifically, in a case where front MC data is generated by selecting three-dimensional MC data related to a partial area of the depth direction from the whole of three-dimensional MC data, the CPU 71 may acquire the size of the corresponding partial area in the depth direction, as a depth measurement range.

Here, in a case where the measurement range D1 is larger than the size of a measurement range which is a reference, since the measurement range in the depth direction increases as compared to the reference, the CPU 71 may calculate a measurement result lower by the increment. Meanwhile, in a case where the measurement range D1 is smaller than the size of the measurement range which is the reference, since the measurement range in the depth direction decreases as compared to a reference eye, the CPU 71 may calculate a measurement result higher by the decrement.

According to the above-described correction, variation in the measurement result according to variation in the size of the measurement range in the depth direction is corrected, and thus it is possible to more quantitatively measure the vascular area. For example, in evaluation of the loss state of blood vessels, in a case of obtaining a measurement value only on the basis of front MC data, information of the depth direction is not considered. Therefore, in a case where the measurement value of blood vessels is constant, even if the size of the measurement range changes, the same result is output. For this reason, evaluation of blood vessel density or the like has room for improvement. According to the above-described configuration, measurement considering change in the measurement range is possible, and it is possible to more suitably obtain blood vessel density or the like. Also, the measurement range in the depth direction may be acquired by two-dimensional positions (for example, sections) where measurement results are acquired, and correction may be performed for each two-dimensional position.

The MC data related to the specific depth area may be OCT front motion contrast data related to a specific layer area, and the CPU 71 may correct a two-dimensional measurement result related to the vascular area in the specific depth area, on the basis of thickness data on the layer area.

More specifically, in a case where the front MC data is acquired on the basis of three-dimensional MC data of the predetermined retina layer (for example, an optic nerve fiber layer (NFL)), the CPU 71 may acquire thickness data of the predetermined retina layer of the subject eye, and correct the measurement result on the basis of the acquired thickness data.

Here, in a case where the retinal thickness of the subject eye is larger than that of reference thickness data (for example, a measurement value of a predetermined retina layer stored in the blood vessel information database and corresponding to normal eye data), since the volume of the predetermined retina layer increases as compared to the data of the reference eye, the CPU 71 may calculate a lower measurement result on the basis of the increment in the thickness. Meanwhile, in a case where the retinal thickness of the subject eye is smaller than that of the reference thickness data, since the volume of the predetermined retina layer decreases as compared to the data of the reference eye, the CPU 71 may calculate a higher measurement result on the basis of the decrement in the thickness. Also, the thickness data of the predetermined retina layer may be acquired on the basis of the OCT data which is the base of the MC data, or may be acquired on the basis of a distance between vascular networks included in the three-dimensional MC data.

According to the above-described correction, change in the measurement result attributable to change in the thickness of a retina layer is corrected, and thus it is possible to more quantitatively measure the vascular area. For example, in evaluation of the loss state of blood vessels, in a case of obtaining a measurement value only on the basis of front MC data, information of the depth direction is not considered. Therefore, in a case where the measurement value of blood vessels is constant, even if the thickness of the retina changes, the same result is output. For this reason, evaluation of blood vessel density or the like has room for improvement. According to the above-described configuration, measurement considering change in the thickness of the retina is possible, and it is possible to more suitably obtain blood vessel density or the like.

For example, in a case where decrease in tissue is faster than decrease in blood vessel density in the early stage of a certain eye disease, if the above-described correction is performed, a blood vessel density result increases. Conversely, for example, in a case where decrease in blood vessel density is faster than decrease in tissue in the early stage of a certain eye disease, if the above-described correction is performed, a blood vessel density result decreases. In this case, follow-up using the corrected measurement result is likely to lead to early detection of the eye disease.

Also, in the above description, as the predetermined retina layer, the NFL has been exemplified. However, the present invention is not limited thereto, and the CPU 71 may apply the above described embodiment to layer areas (such as other retina layers and the choroid layer) of the fundus. A layer area may be an area consisting of a signal layer, or may be an area consisting of a plurality of layers.

Also, according to the above description, a measurement result is corrected in view of the measurement range in the depth direction. However, the present invention is not limited thereto. For example, the CPU 71 may perform three-dimensional measurement on the basis of three-dimensional MC data.

Figure 11:
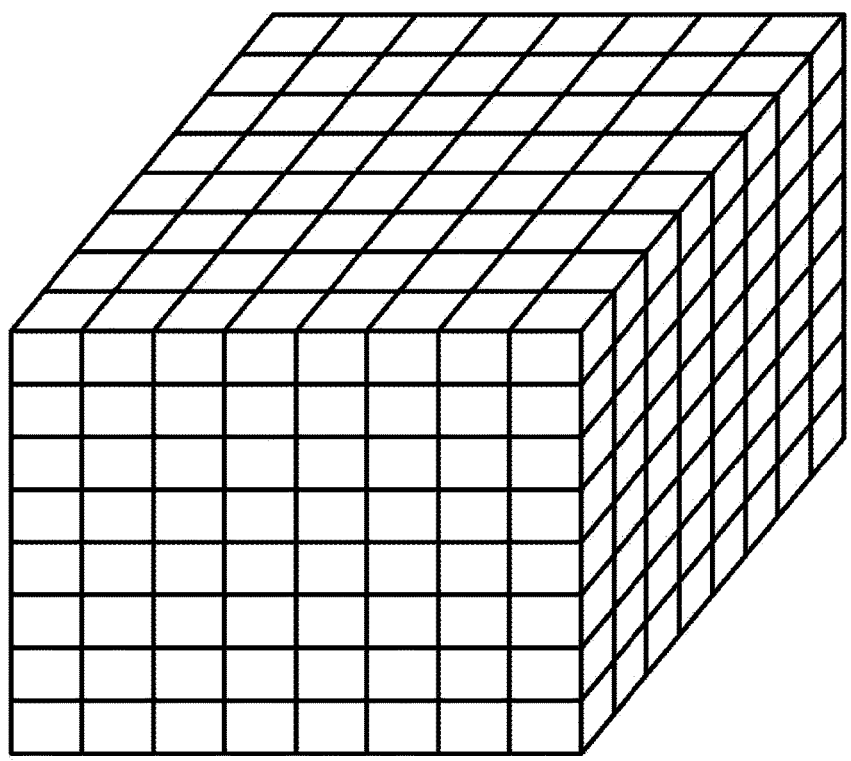
FIG. 11 is a view illustrating an example of a case of three-dimensionally obtaining a distribution of blood vessel measurement results.

More specifically, the CPU 71 may three-dimensionally obtain a distribution of blood vessel measurement results (for example, blood vessel densities). In this case, the CPU 71 may three-dimensionally extract a vascular area of a predetermined depth area (for example, a predetermined retina layer) by processing three-dimensional MC data, and three-dimensionally obtain a measurement result of the extracted vascular area. The CPU 71 may divide the extracted three-dimensional vascular area into a plurality of blocks, and perform a measuring process on each block. In this case, for example, the CPU 71 may acquire a measurement result of each micro area. More specifically, the CPU may acquire a measurement result of each block by dividing three-dimensional 256-by-256-by-256 MC data in units of three-dimensional 8-by-8-by-8 MC data (see FIG. 11 for instance). Also, the CPU 71 may acquire a measurement result of each relatively wide area. More specifically, the CPU may acquire a measurement result of each block by three-dimensionally dividing three-dimensional 256-by-256-by-256 MC data (for example, into three to ten blocks).

A result which is three-dimensionally obtained may be, for example, the volume of a vascular area, or a three-dimensional blood vessel density distribution of a vascular area. In a case of obtaining a three-dimensional blood vessel density distribution, the CPU 71 can obtain the three-dimensional density of a vascular area of a predetermined depth area by obtaining the volume of the vascular area by processing three-dimensional MC data, and dividing the volume of the predetermined depth area included in the three-dimensional MC data by the volume of the vascular area.

The CPU 71 may display the distribution which is the measurement result obtained three-dimensionally, as a color map. For example, the CPU 71 may display a three-dimensional image color-coded according to the measurement results of individual blocks obtained as described above. Also, the CPU 71 may three-dimensionally measure an area surrounded by blood vessels, thereby obtaining a three-dimensional distribution of measurement results related to capillaries. In this case, for example, the CPU 71 may determine continuity of blood vessels by image processing, and extract an area surrounded by blood vessels, on the basis of whether an avascular area is surrounded by blood vessels. In this case, an avascular area does not necessarily need to be three-dimensionally surrounded 360 degrees, and if an avascular area is surrounded to a certain extent, it may be determined as an area surrounded by blood vessels. More specifically, the CPU 71 may calculate the volume of the area surrounded by blood vessels. The CPU 71 may also perform color-coded display of each area according to the calculated volume.

<Display of OCT Blood Vessel Analysis Map and OCT Morphology Analysis Map>

The CPU 71 may display a blood vessel analysis map based on MC data acquired by OCT, and a morphology analysis map based on ophthalmic OCT data, on a monitor, at the same time.

Figure 12:
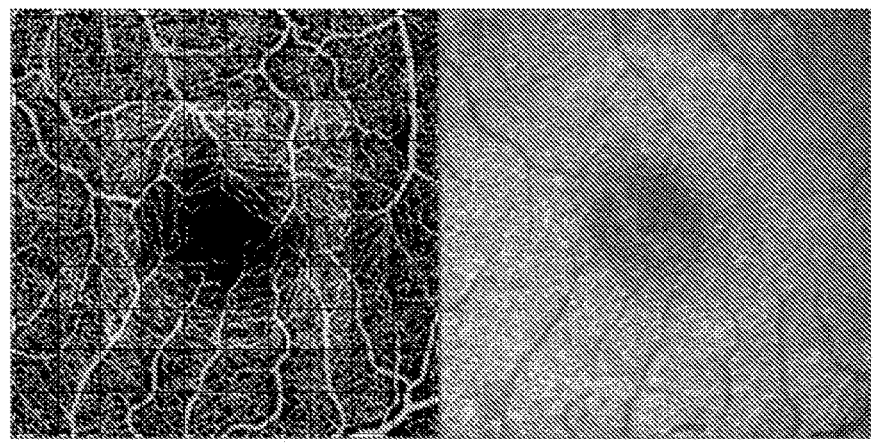
FIG. 12 shows a display example of a blood vessel analysis map and a morphology analysis map.

For example, in a case of displaying a blood vessel analysis map related to a blood vessel measurement result of a subject eye, the CPU 71 may display a morphology analysis map (for example, a map related to the retinal thickness) related to a morphology measurement result of the subject eye (see FIG. 12 for instance). For example, the CPU 71 may display the blood vessel analysis map and the morphology analysis map, side by side.

For example, the CPU 71 may display a blood vessel analysis map and a morphology analysis map with respect to a common layer area of the fundus, at the same time. In this case, it is possible to easily obtain the correlation between blood vessel information and morphology information of the subject eye, with respect to the common area related to the depth direction.

For example, in a case where the thickness of a predetermined retina layer is thin in a morphology analysis map related to the thickness of the retina layer, by checking a blood vessel analysis map at the same time, it is possible to easily grasp whether the decrease in the thickness is attributable to a decrease in blood vessels or to any other factor. In this case, the CPU 71 may acquire blood vessel analysis maps and morphology analysis maps at different measurement times, respectively, in advance, and simultaneously display a blood vessel analysis map and a morphology analysis map in chronological order.

Also, as the type of a blood vessel analysis map, for example, as described above, a basic map, a comparison map, a difference map, and an examination date difference map can be considered. Also, a morphology analysis map may be a map representing a two-dimensional distribution of morphology measurement results related to the fundus. In this case, for example, the morphology analysis map may be a color map color-coded according to measurement values. Examples of an analysis map include a thickness map representing layer thickness (a basic map), a comparison map representing a result of comparison between the layer thickness of a subject eye and the layer thickness of a normal eye stored in the normal eye database, a difference map (a deviation map) representing the standard deviation of deviations between the layer thickness of the subject eye and the layer thicknesses of the normal eyes stored in the normal eye database, and an examination date comparison thickness difference map representing the thickness differences between examination dates.

In a case of obtaining the thicknesses of layers, for example, the OCT data may be divided in units of a layer by performing image processing (for example, a segmentation process) on the OCT data, and the thickness of each layer may be measured on the basis of the intervals between layer boundaries. Obviously, morphology measurement results are not limited to the thicknesses of layers. Also, the analysis map is not limited to a layer thickness map, and may be, for example, a map representing the curvature distribution of the fundus.

Here, in a case where a blood vessel analysis map and a morphology analysis map can be displayed on the display unit 75 at the same time, by displaying maps having the same properties at the same time, it is possible to more suitably perform comparison between morphology information and blood vessel information for its purpose. For example, a basic map which is a blood vessel analysis map and a basic map which is a morphology analysis map may be displayed at the same time. Similarly, comparison maps may be displayed at the same time, and difference maps may be displayed at the same time, and examination date difference maps may be displayed at the same time.

Also, a morphology analysis map may have a display form in which a color map (for example, a map related to layer thickness) is superimposed on a fundus front image. The fundus front image may be acquired by a fundus camera or an SLO, or may be an OCT front image acquired on the basis of OCT data. Also, a morphology analysis map may have a display form in which a color map (for example, a map related to layer thickness) is superimposed on a front MC image.

Also, in a case where a blood vessel analysis map and a morphology analysis map can be displayed at the same time, each map may have a display form in which a color map is superimposed on a front MC image. According to this display, with respect to an image of the MC data, it is possible to easily obtain the correlation between blood vessel measurement results and morphology analysis results. In this case, the MC data, the blood vessel analysis map, and the morphology analysis map may be displayed at the same time. Also, each map may have a form in which a color map is superimposed on a fundus front image. According to this display, with respect to the fundus front image, it is possible to easily obtain the correlation between blood vessel measurement results and morphology analysis results. The fundus front image may be an infrared front image, a color front image, or a front image based on the OCT data.

<Integration of Blood Vessel Measurement Result and Morphology Measurement Result>

Figure 13:
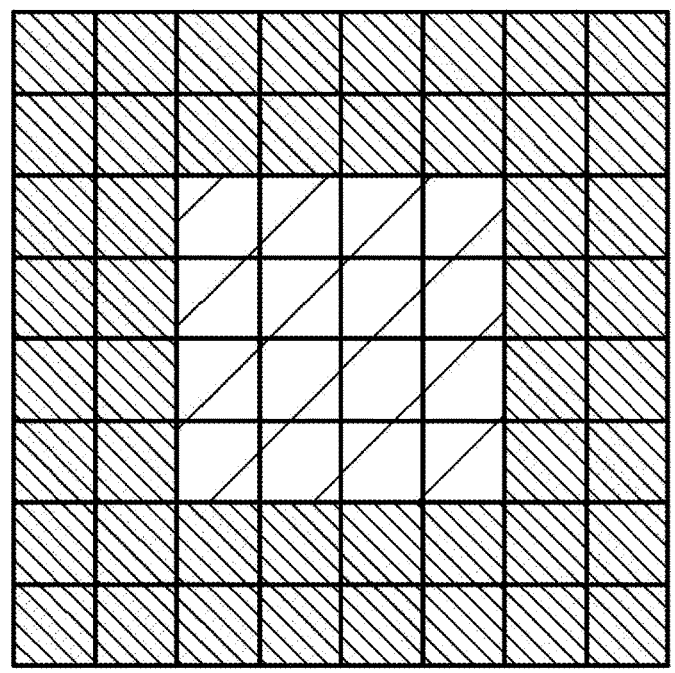
FIG. 13 shows an example of integration of blood vessel measurement results and morphology measurement results.

The CPU 71 may perform a measuring process integrating a blood vessel measurement result of a subject eye and a morphology measurement result of the subject eye. In a case where each measurement result is acquired as a two-dimensional distribution, for example, the CPU 71 may display a result of the integrated measuring process as a single color map or analysis chart (see FIG. 13 for instance). The CPU 71 may also obtain an integrated value as the result of integration of the blood vessel measurement result of the subject eye and the morphology measurement result of the subject eye.

In a case of performing integrated measurement, the CPU 71 may obtain a representative value (for example, the average or the sum) of individual measurement values of the blood vessel measurement result and the morphology measurement result, or may perform weighting calculation by weighting individual measurement values with predetermined factors. In this case, in a case where the units of the individual measurement values do not coincide with each other (for example, density and thickness), a certain integration parameter may be set, and arbitrary coefficients may be set for the blood vessel measurement result and the morphology measurement result.

Also, as described above, the CPU 71 may display a perimetry result of a subject eye and a blood vessel measurement result of the subject eye, on the same screen, at the same time. Also, the CPU 71 may perform a measuring process integrating the perimetry result of the subject eye and the blood vessel measurement result of the subject eye, and display an integrated measurement result.

Obviously, the CPU 71 may display a morphology measurement result of a subject eye, a perimetry result of the subject eye, and a blood vessel measurement result of the subject eye, on the same screen at the same time. Also, the CPU 71 may perform a measuring process integrating the morphology measurement result of the subject eye, the perimetry result of the subject eye, and the blood vessel measurement result of the subject eye, and display an integrated measurement result.

<Blood Vessel Analysis Chart>

Also, according to the above description, a measurement result is displayed as a blood vessel analysis map. However, the present invention is not limited thereto, and a measurement result may be output as a blood vessel analysis chart.

For example, a blood vessel analysis chart may be a blood vessel analysis chart for measuring basic statistics of blood vessel measurement results of preset sections, and a basic statistic of a section may be measured. The number of sections forming a blood vessel analysis chart may be one, or may be two or more. In a case where a blood vessel analysis chart consists of a plurality of sections, a basic statistic may be measured for each section. A basic statistic may be a representative value (such as an average value, a median, a mode, a maximum value, or a minimum value), the degree of scatter (dispersion, standard deviation, or the coefficient of variation), or the like.

For example, a blood vessel analysis chart may be a chart for obtaining the average of each area with respect to a two-dimensional distribution of blood vessel measurement results. A blood vessel analysis chart may have a numerical-value display area for numerically displaying blood vessel measurement results of predetermined areas.

<Follow-Up>

Figure 14:
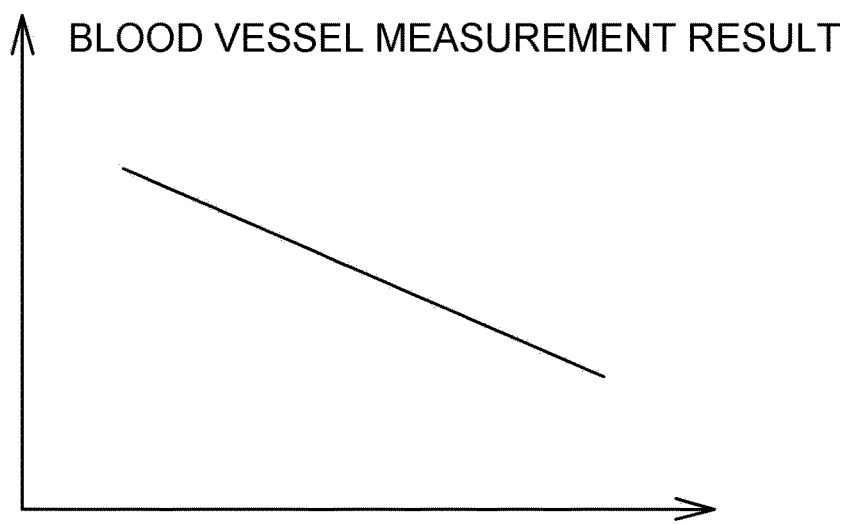
FIG. 14 shows an example of a case of displaying blood vessel measurement results over time.

Also, the CPU 71 may acquire time-series data as a blood vessel measurement result based on MC data from the storage unit 74, and display the acquired blood vessel measurement result over time (see FIG. 14 for instance). For example, the CPU 71 may display a graph representing variation in the blood vessel measurement result with time, or may arrange a plurality of blood vessel analysis maps acquired at different times in chronological order. The plurality of blood vessel analysis maps acquired at different times may be displayed as a time lapse image. With respect to the blood vessel measurement result, the CPU 71 may obtain a difference between a first acquisition time and a second acquisition time. The CPU 71 may obtain a difference between a first acquisition time and a second acquisition time in two-dimensional distributions which are blood vessel measurement results, thereby displaying a difference map of the two-dimensional distributions.

Also, in the above description, the case of performing measurement while alleviating the influence of great blood vessels has been described. However, with respect to the items such as "BLOOD VESSEL ANALYSIS MAP", "BLOOD VESSEL DENSITY MAP", "BLOOD VESSEL INFORMATION DATABASE", "BLOOD VESSEL MEASUREMENT CONSIDERING DEPTH DIRECTION", "DISPLAY OF BLOOD VESSEL ANALYSIS MAP AND THICKNESS ANALYSIS MAP", "INTEGRATION OF BLOOD VESSEL MEASUREMENT RESULT AND MORPHOLOGY MEASUREMENT RESULT", "BLOOD VESSEL ANALYSIS CHART", and "FOLLOW-UP", items to be described below, and technical contents shown in other portions can be embodied with respect to methods applicable to measurement including great blood vessels. Obviously, blood vessel measurement specified for great blood vessels may be performed. Similarly, other items may be embodied in parallel, or may be independently embodied.

Also, in the above description, the MC data acquired by OCT has been described as an example. However, the above-described embodiment can be applied to measurement on fundus blood vessels included in a fundus front image acquired by a fundus imaging device (such as a fundus camera or a scanning Laser ophthalmoscope (SLO)) configured to acquire a fundus front image of a subject eye. In this case, a fundus front image may be at least one of a front image data item (for example, a color fundus image) based on reflected light from a subject eye, and a front image data item based on fluorescent light from a subject eye. Also, analysis using a combination of them with OCT motion contrast data may be performed.

Also, in a case of automatically performing a process of determining a vascular area and an avascular area, the CPU 71 may determine a vascular area and an avascular area by applying a process of binarizing luminance values of the MC data 402 (for example, a discriminant analysis method). Also, in a case where a blood vessel analysis area consists of a plurality of sections, a threshold may be set in units of an area corresponding to a section, or a threshold may be set for the whole of the blood vessel analysis area.

<Development of Blood Vessel Information into MC Data>

The CPU 71 may acquire blood vessel information related to a vascular area included in MC data. Further, the CPU 71 may give the acquired blood vessel information to the vascular area included in the MC data. In this case, it is only required to acquire blood vessel information with respect to at least one blood vessel included in the vascular area. Therefore, with respect to one blood vessel included in the MC data, blood vessel information may be acquired, and the blood vessel information may be given. Also, with respect to a plurality of blood vessels included in the MC data, blood vessel information items may be acquired, respectively, and the blood vessel information items may be given, respectively. Also, blood vessel information may include blood vessel information of each blood vessel, or a set of position information and blood vessel information of each blood vessel may be acquired.

Figure 15:
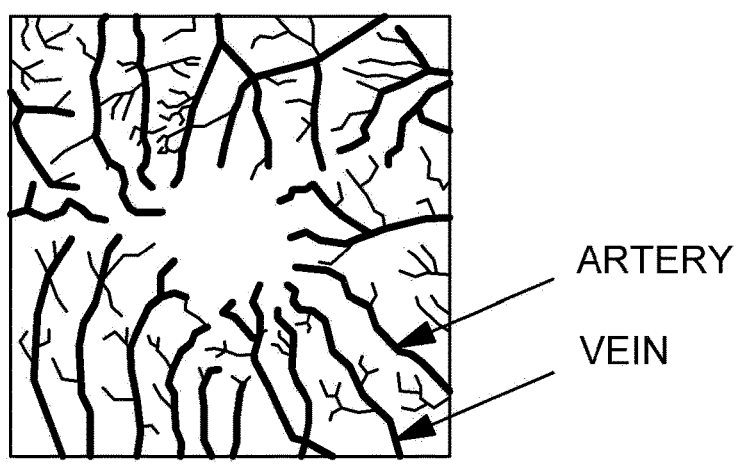
FIG. 15 shows an example of a case of giving arteriovenous information to vascular areas.

With respect to blood vessel information, for example, the CPU 71 may acquire arteriovenous information related to a vascular area included in MC data, as blood vessel information. Further, the CPU 71 may give the arteriovenous information to the vascular area included in the MC data (see FIG. 15 for instance). In short, blood vessel information may be information related to the functions of blood vessels.

Also, for example, the CPU 71 may acquire bleeding information related to a vascular area included in MC data, as blood vessel information. Further, the CPU 71 may give the bleeding information to the vascular area included in the MC data.

In a case of acquiring blood vessel information, the CPU 71 may acquire blood vessel information from data different from MC data. In this case, for example, blood vessel information which is unlikely to be detected only on the basis of MC data can be give to MC data, and evaluation on blood vessels can be better performed by the examiner. The different data may be data having a portion acquired from the same area as that of at least a portion of the MC data. Also, the different data may be distribution data related to blood vessel information, and may be registered with respect to the MC data.

For example, the CPU 71 may acquire blood vessel information from OCT data acquired by OCT or Doppler OCT data. The OCT data or the Doppler OCT data may be data acquired by an OCT device configured to acquire MC data, or may be data acquired by an OCT device different from OCT devices configured to acquire MC data. The CPU 71 may acquire blood vessel information from MC data, and for example, an OCT device for acquiring MC data may use, for example, Doppler OCT.

Also, the CPU 71 may acquire blood vessel information from image data acquired by a modality (an imaging unit) different from OCT. The different modality needs only to be able to acquire blood vessel information, and may be, for example, a fundus camera, an SLO, or an LSFG (Laser speckle flowgraphy) device.

As blood vessel information, besides arteriovenous information and bleeding information, blood flow rate information, layer position information, color information, polarization property information, running-direction information, hardness information, information on the ratio of the inner wall and outer wall of each blood vessel, and the like may be acquired. In short, blood vessel information may be, for example, information related to the property of a vascular area included in MC data. Blood flow rate information may be acquired, for example, by Doppler OCT. Layer position information may be acquired, for example, by OCT data or MC data. Color information may be acquired, for example, by a fundus camera or spectroscopic OCT. Polarization property information may be acquired, for example, by PS-OCT.

When outputting MC data, for example, the CPU 71 may perform image processing on the MC data on the basis of acquired blood vessel information, and display the MC data including the blood vessel information on the display unit 75. However, the present invention is not limited to display on the display unit 75, and the MC data including the blood vessel information may be printed, or may be output an external server. Also, the MC data may be, for example, front MC data, or may be three-dimensional MC data, or may be two-dimensional MC data. In this case, on the basis of blood vessel information given to the MC data in advance, MC data including the blood vessel information may be displayed on the display unit 75. Also, display related to the acquired blood vessel information may be given to the MC data.

When acquiring a measurement result related to a vascular area by analyzing MC data, for example, the CPU 71 may use acquired blood vessel information to acquire a measurement result related to the vascular area. In this case, the CPU 71 may two-dimensionally or three-dimensionally obtain a measurement result. The measurement result may be displayed, for example, as an analysis map, or may be displayed as an analysis chart.

The CPU 71 may use blood vessel information given to MC data in advance, to acquire a measurement result. The CPU may acquire a measurement result related to a vascular area in advance, and then give blood vessel information to the acquired measurement result.

In a case where arteriovenous information is acquired as blood vessel information, the CPU 71 may use the arteriovenous information to acquire at least one of a measurement result related to an artery area and a measurement result related to veins. For example, in a case where bleeding information is acquired as blood vessel information, the CPU 71 may use the bleeding information to acquire a measurement result related to a bleeding vascular area. In short, the CPU 71 may use arteriovenous information of individual blood vessels to perform a measuring process for arteries or for veins.

Also, blood vessel information related to a vascular area included in MC data may be stored together with the MC data in the storage unit 74. In this case, for example, blood vessel information and position information of each blood vessel in the MC data may be stored in association with each other. In this case, a specific storage method is not limited as long as the blood vessel information of at least one blood vessel included in the MC data can be referred to in at least one of the subsequent analyzing/measuring process and the subsequent display process.

As giving of blood vessel information, for example, blood vessel information including position information of individual blood vessels may be registered in MC data such that blood vessel information and individual blood vessels of the MC data are associated with each other. Also, a table representing the correspondence relation between the blood vessel information and the individual blood vessels of the MC data may be set. Also, blood vessel information may be given to MC data of each blood vessel, and the CPU 71 may refer to blood vessel information corresponding to MC data of each blood vessel.

<Acquiring and Giving of Arteriovenous Information>

Hereinafter, an example of a case of acquiring and giving arteriovenous information will be described. For example, the CPU 71 may acquire determination information for determining whether at least one blood vessel included in MC data is an artery or a vein, as arteriovenous information. The arteriovenous information may be arteriovenous information specifying whether each blood vessel is an artery or a vein. Also, the arteriovenous information may be information related to arteries or veins, or may be, for example, information related to only arteries or information related to only veins. The arteriovenous information may be blood vessel distribution information related to arteries and/or veins.

For example, the CPU 71 may perform image processing on MC data on the basis of arteriovenous information, and display the MC data reflecting the arteriovenous information on the display unit 75. In this case, the CPU 71 may display individual vascular areas of the MC data in different colors according to whether each area is an artery or a vein (for example, the CPU may display arteries in red and veins in blue). In this case, colors may be superimposed on blood vessel areas of a black-and-white image of the MC data, or a coloring process may be performed on the MC data. Also, for example, the CPU 71 may display an image of only arteries or veins of the MC data obtained on the basis of the arteriovenous information. In this case, the CPU 71 may use the arteriovenous information to extract artery areas or vein areas, thereby obtaining an image of either the artery areas or the vein areas. Also, the CPU 71 may display MC data related to artery areas, and MC data related to vein areas, switchably or side by side. In this case, arteries and veins may be displayed in different colors. Also, in a case where a specific blood vessel is designated, arteriovenous information may be displayed.

According to the above-described configuration, if whether blood vessels included in MC data are arteries or veins can be specified, it is possible to evaluate the blood vessel state of a subject eye including a function aspect. Therefore, it is thought that the above-described configuration is clinically useful.

Also, if arteriovenous information is given to MC data, display, measurement, and the like of the MC data reflecting the arteriovenous information becomes possible. For example, when acquiring a measurement result related to vascular areas by analyzing MC data, the CPU 71 may acquire at least one of a measurement result related to artery areas and a measurement result related to vein areas. With respect to arteries or veins, as a measurement result, for example, at least one of blood vessel density, blood vessel area, the total quantity of blood vessels, the degree of tortuosity of blood vessels, the regularity of capillaries, and blood vessel diameter may be calculated.

The CPU 71 may acquire an integrated measurement result as the result of integration of a measurement result related to artery areas of MC data and a measurement result related to veins. For example, the CPU 71 may acquire the ratio or difference between the measurement result related to artery areas and the measurement result related to veins. More specifically, the CPU 71 may obtain an arteriovenous ratio (A/V ratio) which is the ratio between the blood vessel diameter of the artery areas and the blood vessel diameter of the vein areas.

With respect to at least one of a measurement result related to artery areas and a measurement result related to veins, the CPU 71 may two-dimensionally or three-dimensionally obtain the measurement result. Further, the CPU 71 may display the obtained measurement result as a blood vessel analysis map on the display unit 75. Also, the CPU 71 may display a blood vessel analysis map related to artery areas and a blood vessel analysis map related to vein areas, switchably or side by side. Obviously, the obtained measurement result is not limited to a blood vessel analysis map, and may be displayed as a blood vessel analysis chart.

Also, the CPU 71 may give arteriovenous information to some or all of blood vessel areas included in MC data, or may give arteriovenous information to a portion of at least one blood vessel, or may give arteriovenous information to the whole of at least one blood vessel. Obviously, the CPU may give arteriovenous information to each of a plurality of blood vessel areas. Further, the CPU 71 may classify individual blood vessel areas by blood vessel diameter, and give arteriovenous information for some blood vessel diameters. For example, the CPU may give arteriovenous information to either capillary areas or great-blood-vessel areas.

As an artery/vein determining method, an artery/vein determining method using OCT, an artery/vein determining method using the principle of a pulse oximeter, a method of performing artery/vein determination on the basis of color information of a color fundus image or an SLO image, or the like can be considered. Hereinafter, specific examples will be described.

<Artery/Vein Determination Based on OCT Data>

In a case of acquiring arteriovenous information, for example, the CPU 71 may acquire arteriovenous information on the basis of OCT data or Doppler OCT data of a fundus acquired by OCT. The OCT data may be, for example, OCT data (for example, two-dimensional OCT data) acquired with respect to areas common to the OCT data and MC data, or may be OCT data which is the base of the MC data. In this case, the OCT data is distinguished from the MC data in that it is fundus reflectance data. The OCT data may be, for example, tomographic image data including morphology information of the fundus.

Figure 16:
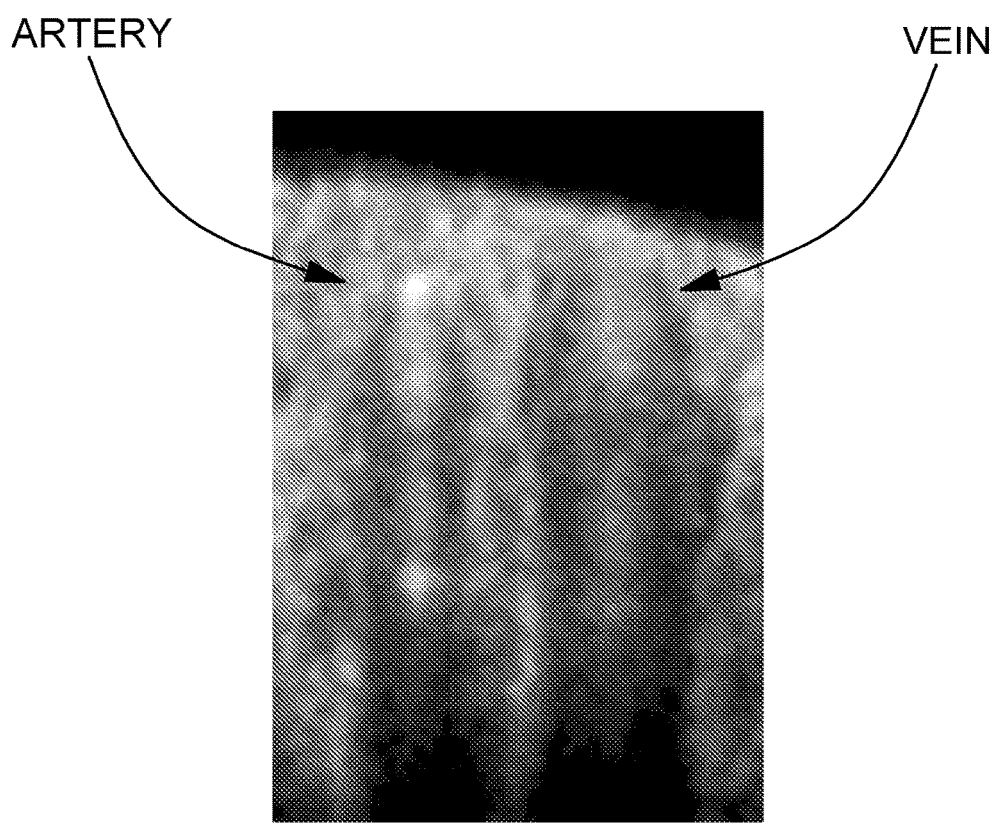
FIG. 16 shows an example of an artery image and a vein image of OCT data.

In a case of acquiring arteriovenous information from OCT data, for example, on the basis of luminance values of the OCT data, whether each blood vessel of a subject eye is an artery or a vein may be determined. More specifically, as shown in FIG. 16, in the OCT data, arteries are displayed bright, and veins are displayed so as to be darker than the arteries.

In a case of detecting a vascular areas of OCT data, for example, with respect to A-scan data, luminance values of areas closer to the NFL side than to the RPE side may be obtained, and areas having relatively small luminance values may be set as candidates for a vascular area. Form the blood vessel candidate areas, the CPU 71 may detect areas having a predetermined width or greater in a scan direction, as vascular areas. Also, in a case of detecting vascular areas in the OCT data, the CPU 71 may detect the vascular areas of the OCT data using blood vessel information included in the MC data. In this case, in a case where the OCT data which is used is OCT data which is the base of the MC data, registration between the data is easy, and it is possible to easily specify the vascular areas.

Figure 17:
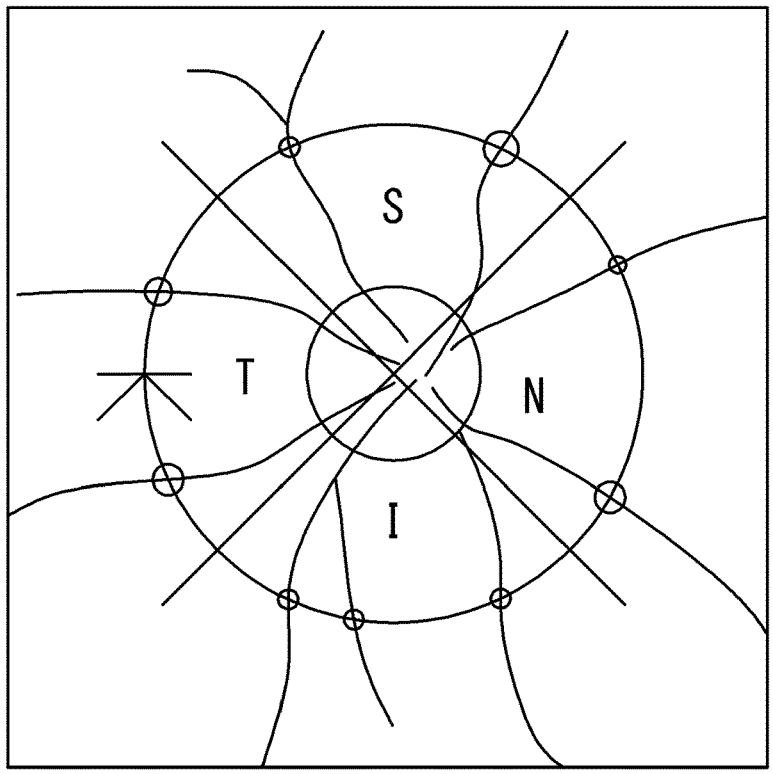
FIG. 17 shows an example of a case of determining arteries and veins on the basis of luminance values of vascular areas on OCT data.

Subsequently, the CPU 71 may perform artery/vein determination on the basis of the luminance values of the vascular areas of the OCT data. For example, the CPU 71 may perform artery/vein determination using the luminance average of vascular areas of each of TSNIT areas of the fundus as shown in FIG. 17. With respect to each of the TSNIT areas, the CPU 71 may calculate the luminance average of the ILM to IPL/INL of each vascular area, and determine a threshold at which interclass variance becomes maximum, by a discriminant analysis method. The CPU 71 may determine blood vessels having luminance higher than the threshold, as arteries, and determine vessels having luminance lower than the threshold, as veins.

However, the method of performing artery/vein determination on OCT data is not limited thereto, and may use a difference in the wall luminance between arteries and veins. Also, the method may use a difference in the luminance of lower-side RPE between arteries and veins. In short, the artery/vein determining method is not particularly limited as long as it uses a difference in an image of OCT data between arteries and veins (for example, a luminance difference or a shape difference). In other words, the inventors of the present invention found a determining method using a difference in the drawing state between arteries and veins of blood vessels included in OCT data.

If arteriovenous information based on OCT data is acquired in the above-described way, the CPU 71 may give the arteriovenous information to corresponding vascular areas of MC data which are areas common to the MC data and the OCT data. Also, in a case of three-dimensional MC data, the CPU 71 may acquire arteriovenous information on the basis of individual two-dimensional OCT data items forming the three-dimensional OCT data, and give the acquired arteriovenous information to blood vessels corresponding to the individual two-dimensional MC data of the three-dimensional MC data. Obviously, the CPU 71 may acquire three-dimensional distribution information on arteries or veins included in three-dimensional OCT data, and give arteriovenous information based on the acquired three-dimensional distribution information to vascular areas of the three-dimensional MC data. In this case, the CPU 71 may acquire arteriovenous information using front OCT data, and give the acquired arteriovenous information to vascular areas of the front OCT data.

Also, according to the above description, arteriovenous information is acquired on the basis of OCT data. However, the present invention is not limited thereto, and arteriovenous information may be acquired using whether a phase change amount in Doppler OCT data is positive or negative. For example, the CPU 71 may obtain a blood flow direction on the basis of the phase change amount, and acquire arteriovenous information on the basis of the blood flow direction. In this case, for example, the CPU may determine an area where the blood flow direction leads to the optic disc, as a vein, and determine an area where the blood flow direction leads to the opposite side to the optic disc, as an artery.

<Use of Principle of Pulse Oximeter>

A pulse oximeter measures the oxygen saturation of blood using a difference in absorption of red light and infrared light between deoxygenated hemoglobin and oxygenated hemoglobin. This principle is used to perform the same measurement of that of a pulse oximeter with an OCT light source. An area having high oxygen saturation is determined as an artery, and an area having lower oxygen saturation is determined as a vein.

In other words, the CPU 71 may acquire arteriovenous information on the basis of oxygen saturation data of a subject eye. In this case, the obtained arteriovenous information of individual blood vessels and MC data may be registered, whereby the arteriovenous information may be given.

<Acquiring of Arteriovenous Information from Another Device>

The CPU 71 may acquire arteriovenous information on the basis of image data acquired by an imaging means (a modality) different from OCT. Image data which is acquired by another modality such as a fundus camera, an SLO, an LSFG (Laser speckle flowgraphy) device may be used. For example, on the basis of a difference in color tone between arteries and veins in a fundus image acquired by a fundus camera or an SLO, arteriovenous information may be acquired. Also, artery/vein determination may be performed using a characteristic in which the color of arteries is brighter than that of veins.

Also, on the basis of a difference in the blood flow direction attributable to temporal change in a fluorescent contrast image which is acquired by an SLO or a fundus camera, arteriovenous information may be acquired. Also, on the basis of a difference in relative blood flow rate or blood flow direction which is acquired by LSFG, arteriovenous information may be acquired.

Also, in a case of acquiring arteriovenous information in the above-described way, an OCT optical system and a modality for acquiring an image to be the base of arteriovenous information may be disposed, and simultaneously with acquisition of motion contrast data, an image of them may be acquired. However, the present invention is not limited thereto, and the modality may be disposed separately from the OCT device. Also, the CPU 71 does not necessarily need to perform a determining process in the above-described way, and the CPU 71 may acquire arteriovenous information acquired in advance, from the outside or the storage unit 74.

<Measurement of Blood Vessel Direction>

With respect to three-dimensional MC data, the CPU 71 may calculate edge strength with respect to each direction of three directions, and acquire running-direction information related to vascular areas, on the basis of the edge strengths of the individual directions. Further, the CPU 71 may give the acquired running-direction information to vascular areas included in the three-dimensional MC data. In this way, it is possible to detect the direction of each blood vessel included in MC data, and thus it is possible to easily perform measurement on the degree of tortuosity or the like.

Figure 18:
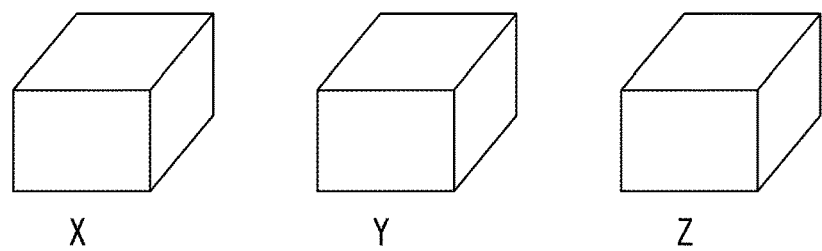
FIG. 18 is a view illustrating an example of a case of acquiring running-direction information.

More specifically, as shown in FIG. 18, the CPU 71 may perform edge detection on volume data of three-dimensional MC data with respect to X, Y, and Z directions, and acquire the edge detection result related to each of the X, Y, and Z directions as volume data. In this case, the volume data which are the edge detection results related to the individual directions are individually acquired. Here, on the basis of the edge detection results of the volume data corresponding to individual points of the three-dimensional MC data, it is possible to easily detect the running direction of each blood vessel. For example, in a case where only blood vessels straightly extending in the X direction exist in the three-dimensional MC data, since edges are detected in the Y and Z directions, but any edge is not detected in the X direction, on the basis of this, the running direction is detected. This relation can be used to detect the running direction of each blood vessel. Although a simple example has been described for convenience of explanation, obviously, even in a case where a plurality of blood vessels run in different directions, the above-described method can be applied.

Figure 19:
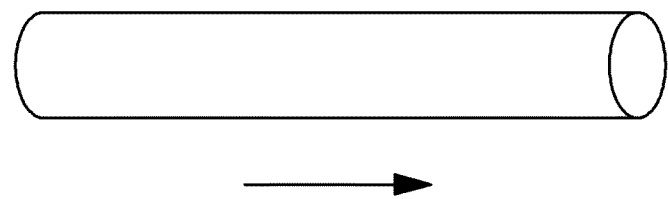
FIG. 19 shows an example of a case of displaying three-dimensional motion contrast data reflecting running-direction information on a display unit.

The CPU 71 may perform image processing on three-dimensional motion contrast data on the basis of the acquired running-direction information, and display the three-dimensional motion contrast data reflecting the running-direction information on the display unit (see FIG. 19 for instance). In this case, an arrow may be displayed next to each blood vessel, or colors according to running directions may be imparted.

In a case of acquiring a measurement result related to vascular areas by analyzing three-dimensional motion contrast data, the CPU 71 may use running-direction information to acquire the degree of tortuosity of each blood vessel.

However, the above-described running-direction detection is not limited to three-dimensional detection, and may be applied to two-dimensional detection. For example, edge detection may be performed on front MC data with respect to each of the X and Y directions, and on the basis of the edge detection results, running directions may be two-dimensionally detected.

However, the present invention is not limited to the above-described method, and running-direction detection may be performed by performing a thinning process on individual blood vessels of MC data and obtaining continuity of individual pixels of skeletons generated by the thinning process. For example, two-dimensional running-direction detection may be performed by obtaining continuity of each pixel with eight neighboring pixels. Similarly, three-dimensional running-direction detection may be performed by three-dimensionally obtaining continuity of each pixel with neighboring pixels.

<Running State of Blood Vessel Related to Fundus Layer>

Figure 20:
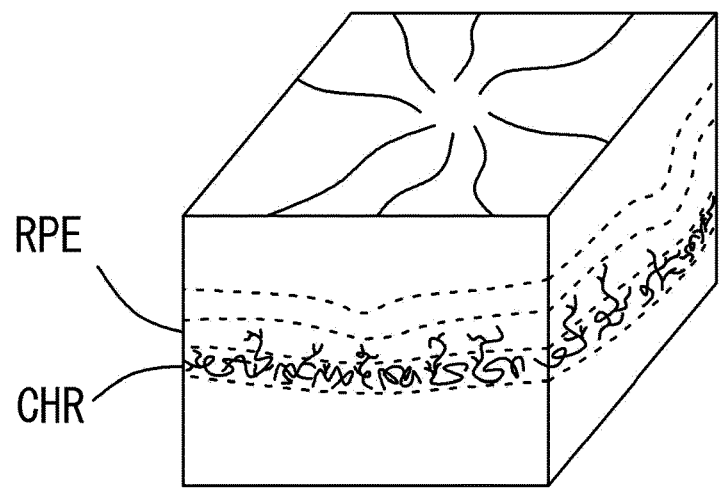
FIG. 20 shows an example of a case of obtaining the running states of blood vessels in layer areas.

The CPU 71 may acquire layer running information representing the running states of individual vascular area included in MC data with respect to a layer area formed in a subject eye (see FIG. 20 for instance). Further, the CPU 71 may give the layer running information to the vascular areas included in the MC data. In this case, for example, it is possible to acquire the running states of blood vessels related to a layer area, and it is possible to determine whether a subject eye is normal or abnormal.

The layer running information may be, for example, information capable of identifying a layer area where at least one blood vessel included in the MC data is running. The layer running information may be, for example, information on whether at least one blood vessel included in the MC data is running in a specific layer area. Also, the layer running information may be information representing that at least one blood vessel included in the MC data is running from which layer area to which layer area.

MC data may be MC data related to a plurality of layers formed at the fundus of a subject eye, and the CPU 71 may perform a process of specifying each layer where at least one blood vessel runs, among the plurality of layers, thereby acquiring layer running information.

More specifically, the CPU 71 may acquire layer running information on the basis of the running positions of blood vessels of MC data, and layer positions acquired by performing a segmentation process on the MC data or OCT data.

For example, the CPU 71 may compare three-dimensional position information of specific blood vessels included in MC data with three-dimensional position information of each layer of the fundus, thereby specifying a fundus layer where a blood vessel K runs. In this case, the CPU 71 may specify the fundus layer where the blood vessel K runs, by determining whether the blood vessel K runs in each specific layer. For example, it is detected that the blood vessel K existing in a choroid layer reaches the RPE layer.

In this case, the CPU 71 may determine whether each blood vessel distributed in a first layer (for example, a choroid layer) reaches (extends to) a second layer (for example, the RPE layer) different from the first layer. Also, the CPU 71 may obtain whether each blood vessel area of MC data reaches from the first layer to a certain layer. According to the above-described method, since it is possible to easily determine whether each blood vessel existing in a choroid layer reaches the RPE layer, it is possible to easily perform evaluation related to diabetic retinopathy and so on.

In the above-described way, the CPU acquires layer running information related to individual blood vessels included in MC data, thereby capable of giving the layer running information to the individual blood vessels. The CPU 71 may perform image processing on three-dimensional motion contrast data on the basis of the given layer running information, and display the three-dimensional motion contrast data reflecting the layer running information on the display unit. In this case, colors according to the layer running information may be imparted.

On the basis of the given layer running information, the CPU 71 may acquire measurement results of the blood vessels. For example, the CPU 71 may acquire a two-dimensional distribution of blood vessels existing in the first layer and reaching the second layer, as a measurement result, and may acquire a density distribution or the like specifying the corresponding blood vessels. Also, the CPU 71 may acquire the measurement results related to blood vessels included in the MC data and crossing a plurality of layers.

The CPU 71 may two-dimensionally or three-dimensionally obtain blood vessel measurement results based on the layer running information. Further, the CPU 71 may display the obtained measurement results as a blood vessel analysis map on the display unit 75. Obviously, the obtained measurement result is not limited to a blood vessel analysis map, and may be displayed as a blood vessel analysis chart.

<Separation of Blood Vessel Layers Using Motion Contrast Data>

The CPU 71 may acquire blood vessel distribution information on two-dimensional abundance of blood vessels in each depth area of three-dimensional MC data. Further, on the basis of the acquired blood vessel distribution information, the CPU 71 may separate the blood vessels included in the three-dimensional MC data, in units of a layer. In other words, the CPU may separate blood vessel layers using the MC data.

In this way, it is possible to surely separate the blood vessel layers. Meanwhile, in a technology according to the related art, separation of blood vessel layers of MC data is performed using layer boundary detection results of OCT data. For example, the blood vessel layer of NFL is determined by a fixed value, like a predetermined range of the layer boundary between NFL and GCL. Therefore, it is impossible to suitably separate blood vessel layers of some patients. Also, in a case where layer boundary detection of OCT fails, there is a possibility that separation of blood vessel layers will fail. Blood vessels of the retina are concentrated in specific areas. For this reason, it can be considered that it is possible to accurately separate blood vessel layers by separating a result of OCT angiography into blood vessel groups.

Figure 21:
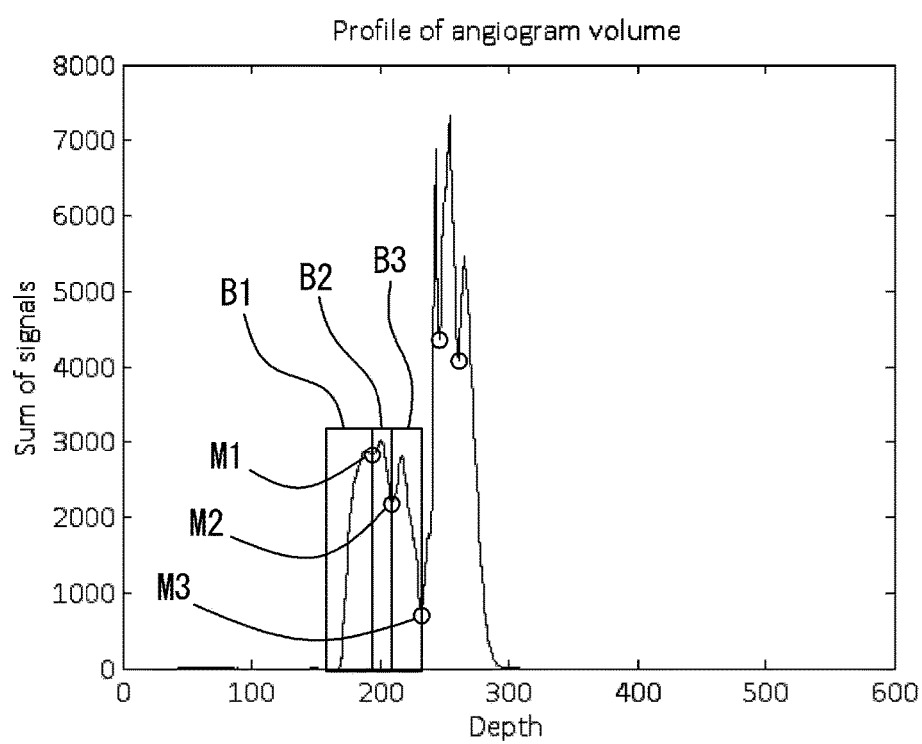
FIG. 21 shows an example of a case of separating blood vessel layers using motion contrast data.

More specifically, for example, with respect to front MC data of each of depth areas, the number of pixels where blood vessels has been detected may be measured as two-dimensional abundance of blood vessels, and a histogram representing a distribution of the numbers of blood vessel pixels of the individual depth areas may be acquired (see FIG. 21). Also, the CPU 71 may obtain the blood vessel density distribution or blood vessel area of front MC data of each depth area, as two-dimensional abundance of blood vessels. In other words, blood vessel distribution information may be, for example, information representing a two-dimensional abundance distribution of blood vessels of each depth area of three-dimensional MC data with respect to the depth direction.

Also, the CPU 71 may measure the number of pixels where blood vessels have been detected, as two-dimensional abundance of blood vessels, and may acquire a histogram representing a distribution of the numbers of pixels of the individual depth areas. Also, in a case of dividing three-dimensional MC data with respect to the depth direction, the CPU may divide the three-dimensional MC data in units of a pixel or in units of two or more pixels.

In general, blood vessels of a fundus are distributed to individual layers of the fundus and form blood vessel layers. Therefore, the acquired blood vessel distribution information includes peaks according to the individual blood vessel layers. For this reason, the CPU 71 may separate the blood vessels in units of a layer by separating them by the peaks of the blood vessel distribution information. Also, in the case of separating the blood vessels by the peaks of the blood vessel distribution information, for example, the CPU 71 may detect the peaks according to whether each area having abundance exceeding predetermined abundance has a predetermined width in the depth direction.

Also, the CPU may divide three-dimensional MC data into a plurality of areas with respect to the direction of the front (a direction perpendicular to the depth direction), and acquire blood vessel distribution information of the individual areas. In this case, with respect to each area, the CPU may separate blood vessels in units of a layer. For example, individual blood vessel layers may be separated in units of blocks B1, B2, and B3 of FIG. 21.

Also, the CPU 71 may give layer running information making it possible to distinguish blood vessels of each layer from blood vessels of the other layers, to the corresponding layer.

<Acquiring and Giving of Bleeding Information>

The CPU 71 may acquire bleeding information related to vascular areas included in MC data. Further, the CPU 71 may give the acquired bleeding information to blood vessel areas included in the MC data.

The bleeding information may be position information of bleeding areas of the vascular areas. Also, the bleeding information may be bleeding information for determining whether at least one blood vessel has bled or not. Also, the bleeding information may be bleeding information specifying whether each blood vessel has bled or not. Also, the bleeding information may be information representing a distribution of bleeding areas.

The bleeding information may be acquired, for example, on the basis of front OCT data. The front OCT data may be front OCT data related to a portion of the depth direction of three-dimensional OCT data, or may be front OCT data related to the whole of the depth direction of the three-dimensional OCT data. Obviously, bleeding information may be acquired on the basis of two-dimensional OCT data. In this case, position information of the bleeding information may be acquired.

Figure 22:
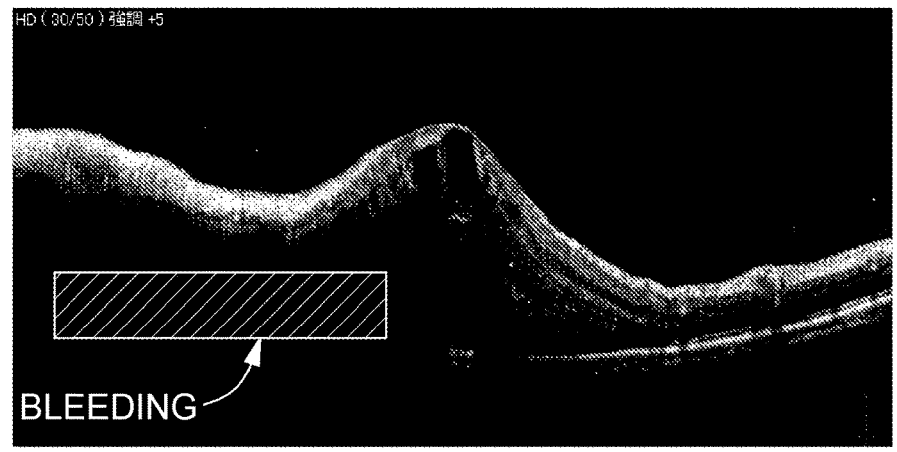
FIG. 22 shows an example of a bleeding area in OCT data.

In OCT data, with respect to bleeding areas where blood vessels have bled, the rear sides from the bleeding areas have small luminance values, and thus layer structures are not drawn. Also, in an example of FIG. 22, in the left area of an image, bleeding occurs. Therefore, those characteristics can be used to detect bleeding areas, whereby it is possible to determine position information of the bleeding areas.

Figure 23:
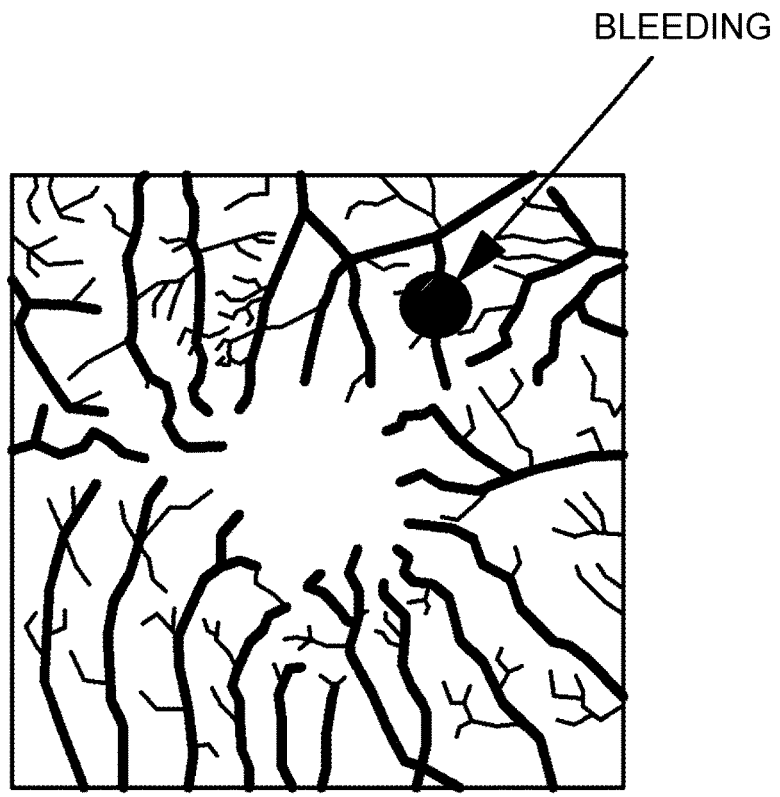
FIG. 23 shows an example of display of MC data having a bleeding area.

Here, information on the blood vessel areas acquired by OCT data may be given to MC data. In this case, on the basis of the bleeding area information given to the MC data, the CPU 71 may display the MC data reflecting the given bleeding area information (see FIG. 23 for instance). In this way, it is possible to check bleeding areas where bleeding has occurred in MC data. In this case, the position information of the bleeding areas and position information of the MC data are associated with each other, whereby the positions of the bleeding areas are registered on the MC data.

In this case, as the MC data reflecting the bleeding areas, for example, MC data having graphics corresponding to the bleeding areas, or MC data in which blood vessel areas related to the bleeding areas can be determined may be displayed. Also, the bleeding information may be acquired from an image acquired by any other imaging means such as a fundus camera or an SLO.

<Giving of Label>

During analysis and display of three-dimensional data, the CPU 71 may give labels representing analysis results, to individual voxels of the three-dimensional data. The type of label may be at least one of types "VASCULAR AREA", "AVASCULAR AREA", "BLOOD FLOW", "BLOOD VESSEL WALL", "DIRECTION OF BLOOD VESSEL", "VASCULAR LAYER AND DEPTH", "BLOOD FLOW VOLUME", "BLOOD FLOW RATE", "OXYGEN SATURATION OF BLOOD FLOW", "CONNECTION OF BLOOD VESSELS", "NORMAL BLOOD VESSEL", "ABNORMAL BLOOD VESSEL", "BLEEDING", and the like.

The label may be represented by a numerical value, or may be represented by a color or a graph. Also, the label may be displayed alone, or may be displayed on OCT data (a tomographic image), a fundus front image, or OCT MC data (an OCT angiography image). Alternatively, a combination of a plurality of labels may be displayed. Further, the CPU 71 may perform artery/vein determination on the basis of OCT data or OCT MC data acquired by any other device as described above, and record the determination results as labels for individual voxels.

Further, the CPU 71 may determine the directions of blood vessels, and record the determination results as labels for voxels. More specifically, the CPU may perform edge detection in the X, Y, and Z directions, and detect the directions of blood vessels on the basis of the magnitudes of edge components of the individual directions, and record the directions as labels. The CPU may calculate the degree of tortuosity of each blood vessel on the basis of the labels representing the directions of the blood vessels, and record the degree of tortuosity as a label. As a method of calculating the degree of tortuosity, a method of calculating the degree of tortuosity by accumulating a difference in the blood vessel direction label between a previous voxel and a current voxel while tracing each blood vessel can be considered.

Further, the CPU 71 may determine whether each blood vessel is normal or abnormal by checking connections of blood vessels. For example, if a blood vessel from a choroid layer extends toward NFL, it is determined as being abnormal. If labels "NORMAL BLOOD VESSEL" and "ABNORMAL BLOOD VESSEL" are given, it is possible to display either the label "NORMAL BLOOD VESSEL" or the label "ABNORMAL BLOOD VESSEL", or display the labels "NORMAL BLOOD VESSEL" and "ABNORMAL BLOOD VESSEL" in different colors.

Further, the CPU 71 may record layer information of blood vessel layers as labels for voxels. In other words, if results of blood vessel layer separation using MC data are given as labels for voxels, it is possible to use the labels to display the blood flow of each layer or perform normality/abnormality determination on blood vessels to be described below.

Figure 24:
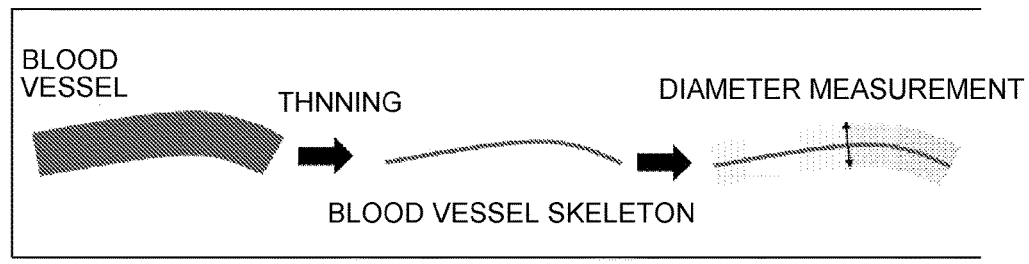
FIG. 24 is a view illustrating an example of a thinning process.

During measurement of blood vessel diameters, the CPU 71 performs thinning on areas having a label "VASCULAR AREA", and record a label "BLOOD VESSEL SKELETON" for voxels of the thinned area (see FIG. 24). Further, the CPU 71 may measure a change in each blood vessel caused by thinning, as the diameter of the blood vessel, and record the blood vessel diameter as a label for voxels.

More specifically, the CPU may perform thinning on vascular areas detected by MC data, and measure the original blood vessel diameters from the thinned lines. The results of thinning and the blood vessel diameters may be recorded for voxels. Blood vessel skeletons may be displayed by displaying only voxels having a label "THINNING". Also, a label "BLOOD VESSEL DIAMETER" may be used to display either blood vessels having a predetermined blood vessel diameter or greater, or blood vessels having a predetermined blood vessel diameter or less, in different colors according to the blood vessel diameters. Also, a database on eyes having normal blood vessel diameters may be constructed.

Further, the CPU 71 may determine bleeding portions from OCT data and OCT MC data, and record a label for voxels. In the OCT data, bleeding portions have relatively high reflectance. Also, on the lower sides from bleeding portions, signals attenuate. The combination of this information and the OCT MC data may be used to detect portions having the features of bleeding portions and included in vascular areas, as bleeding portions, and record a label.

Also, labels may be displayed in chronological order for follow-up. Also, combinations of labels and examination results of any other device may be displayed.

Figure 25:
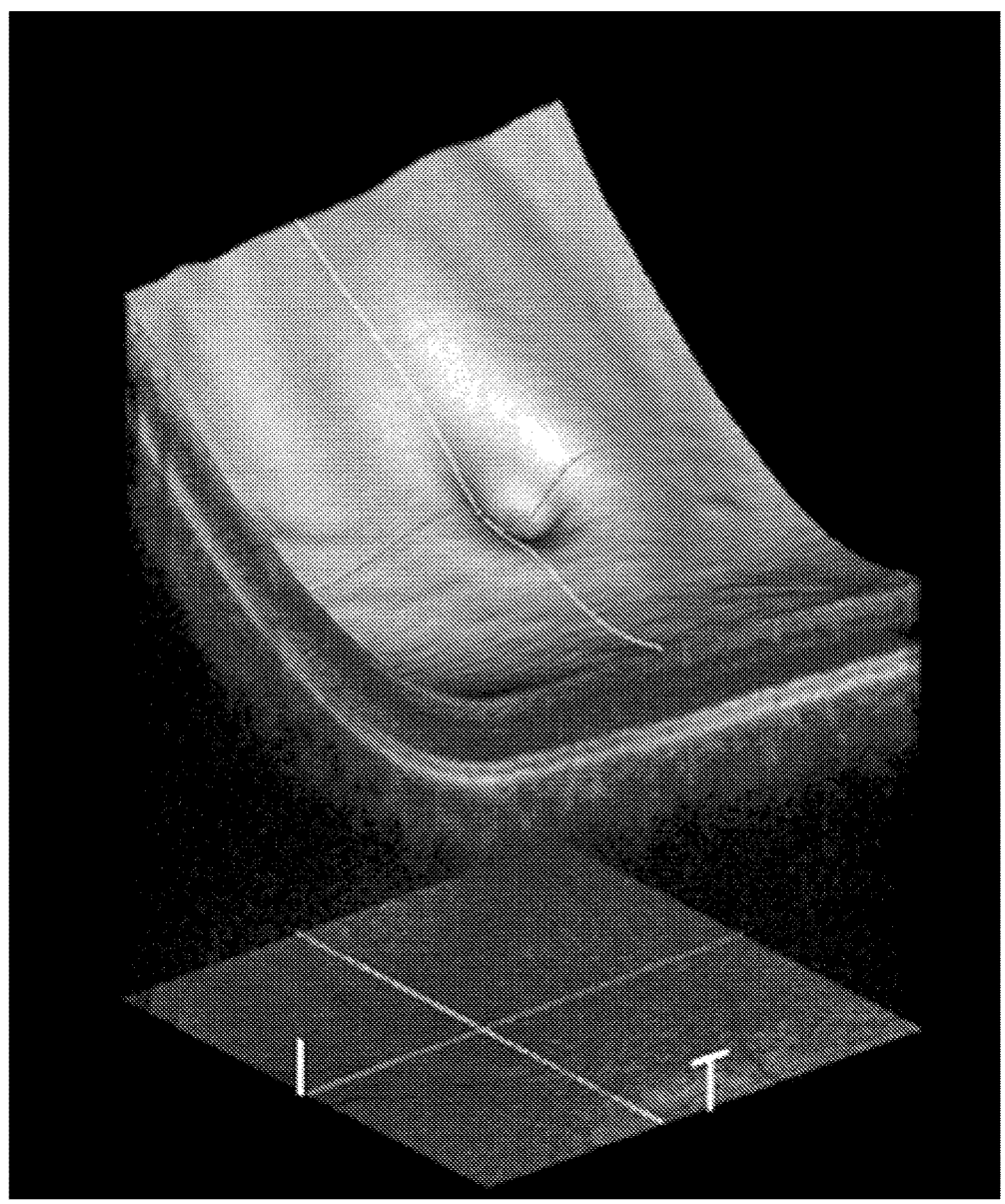
FIG. 25 shows an example of a case where an OCT label is selected as a display label.

FIG. 25 shows an example of a case where an OCT label is selected as a display label, and data like a 3D map is displayed. Here, for each voxel, various analog RGB signal may be given, and one or more labels desired by the examiner may be displayed on three-dimensional data.

Here, if a level "BLOOD VESSEL" is selected, only blood vessels of the retina can be displayed, whereby the structure of the blood vessels can be easily confirmed. Further, the label "BLOOD VESSEL" and a label "LAYER" may be combined, whereby individual layers may be displayed in different colors.

The CPU 71 may combine the label "BLOOD VESSEL" and a label "ARTERY", thereby displaying arteries and veins in different colors. Also, either arteries or veins may be displayed. Further, the CPU may combine the label "BLOOD VESSEL", the label "ARTERY", and a label "LAYER BOUNDARY", thereby displaying blood vessels of only a desired retina layer.

In this way, a plurality of labels is combined, whereby it is possible to easily confirm a variety of data. Also, the examiner can freely set combinations of labels. Further, results of any other device may be additionally displayed. For example, by combining perimetry results and OCT angiography results, it is possible to confirm the correction between perimetry loss and blood vessel loss.

According to label display as described above, it is possible to assist diagnosis by analyzing a variety of data including OCT data, MC data, and the like as three-dimensional data, and presenting the analysis result to a user.

Also, in the above description, the fundus of the subject eye has been described. However, the present invention is not limited thereto, and can be applied to the anterior eye part of the subject eye. Further, the present invention is not limited to the subject eye, and can also be applied to other motion contrast data (for example, motion contrast data of tissues other than eyes) acquired by OCT.

The present disclosure discloses the following configurations:

(1) An ophthalmic analysis device for analyzing OCT motion contrast data including blood vessel information of a subject eye acquired by an ophthalmic OCT, comprising:

an analysis processing means configured to analyze the OCT motion contrast data, thereby acquiring a measurement result related to a capillary area of the subject eye, wherein the analysis processing means executes an alleviating process for alleviating the influence of great blood vessels having blood vessel diameters larger than those of capillaries on the measurement result to acquire the measurement result related to the capillary area.

(2) The ophthalmic analysis device according to (1), wherein:

as the alleviating process, a process of specifying the capillary area of the OCT motion contrast data is performed, and on the basis of the specified capillary area, the measurement result related to the capillary area is acquired.

(3) The ophthalmic analysis device according to (1), wherein:

in the alleviating process, in the OCT motion contrast data, an area surrounded by blood vessels is specified on the basis of a vascular area included in the OCT motion contrast data, and on the basis of the specified area, the measurement result related to the capillary area is acquired.

(4) The ophthalmic analysis device according to any one of (1) to (3), wherein:

front image data based on reflected light from the subject eye, and/or front image data based on fluorescent light from the subject eye is analyzed, whereby the measurement result related to the capillary area of the subject eye is acquired.

(5) The ophthalmic analysis device according to any one of (1) to (4), wherein:

as the measurement result related to the capillary area, blood vessel density of the capillary area is acquired.

(6) The ophthalmic analysis device according to any one of (1) to (5), wherein:

the measurement result related to the capillary area is obtained two-dimensionally or three-dimensionally.

(7) The ophthalmic analysis device according to any one of (1) to (6), wherein:

a color map color-coded according to measurement results of individual positions related to the capillary area is displayed.

(8) The ophthalmic analysis device according to any one of (1) to (7), further comprising:

a blood vessel information database based on the measurement result related to the capillary area acquired through the alleviating process.

(9) The ophthalmic analysis device according to any one of (1) to (8), wherein:

the OCT motion contrast data is analyzed, whereby a measurement result related to a vascular area included in a specific depth area is acquired, and on the basis of a measurement range of the depth area, the measurement result is corrected.

(10) The ophthalmic analysis device according to any one of (1) to (9), wherein:

a blood vessel analysis map based on OCT motion contrast data acquired by ophthalmic OCT, and a morphology analysis map based on OCT data acquired by ophthalmic OCT are displayed on a monitor at the same time.

(11) The ophthalmic analysis device according to any one of (1) to (10), wherein:

an integrated measurement process which is a measuring process of integrating a blood vessel measurement result based on OCT motion contrast data acquired by ophthalmic OCT, and a morphology measurement result based on OCT data acquired by ophthalmic OCT is performed.

(12) The ophthalmic analysis device according to any one of (1) to (11), wherein:

time-series data which is a blood vessel measurement result based on OCT motion contrast data is acquired from a storage unit, and the acquired blood vessel measurement result is displayed over time.

(13) The ophthalmic analysis device according to any one of (1) to (12), wherein:

arteriovenous information on the vascular area included in the OCT motion contrast data is acquired, and the arteriovenous information is given to the vascular area.

(14) The ophthalmic analysis device according to (13), wherein:

the arteriovenous information based on data acquired by ophthalmic OCT is acquired.

(15) The ophthalmic analysis device according to any one of (1) to (14), wherein:

the subject eye data is three-dimensional OCT motion contrast data, and with respect to three-dimensional OCT motion contrast data, edge strengths are calculated in three directions, respectively, and on the basis of the edge strengths of the individual directions, running-direction information on the vascular area included in the three-dimensional OCT motion contrast data is acquired, or with respect to three-dimensional OCT motion contrast data, a thinning process is performed with respect to each direction of three directions, and the running-direction information is acquired from a skeleton of the thinning process, and the running-direction information is given to the vascular area.

(16) The ophthalmic analysis device according to any one of (1) to (15), wherein:

layer running information representing a running state of a vascular area included in the OCT motion contrast data with respect to a layer area formed at the subject eye is acquired, and the layer running information is given to the vascular area.

(17) The ophthalmic analysis device according to (16), wherein:

bleeding information on the vascular area included in the OCT motion contrast data is acquired, and the bleeding information is given to the vascular area.

(18) An ophthalmic analysis device for analyzing OCT motion contrast data including a vascular area of a subject eye, comprising:

an analysis processing means for analyzing the OCT motion contrast data, wherein the analysis processing means acquires arteriovenous information on the vascular area included in the OCT motion contrast data, and the arteriovenous information is given to the vascular area.

(19) The ophthalmic analysis device according to (1), wherein:

the analysis processing means acquires the arteriovenous information based on data acquired by OCT.

(20) An ophthalmic analysis device for analyzing subject eye data including blood vessel information of a subject eye, comprising:

an analysis processing means configured to analyze the subject eye data, thereby acquiring a measurement result on a capillary area, wherein the analysis processing means acquires the measurement result on the capillary area through an alleviating process for alleviating the influence of great blood vessels having blood vessel diameters larger than those of capillaries on the measurement result.

(21) The ophthalmic analysis device according to (20), wherein:

the analysis processing means performs a process of specifying the capillary area included in the subject eye data, as the alleviating process, and on the basis of the specified capillary area, the analysis processing means acquires the measurement result on the capillary area.

(22) The ophthalmic analysis device according to (20), wherein:

the analysis processing means specifies an area surrounded by blood vessels in the subject eye data, on the basis of a vascular area included in the subject eye data, as the alleviating process, and on the basis of the specified area, the analysis processing means acquires the measurement result on the capillary area.

(23) The ophthalmic analysis device according to any one of (20) to (22), wherein:

the subject eye data is at least one of OCT motion contrast data, front image data based on reflected light from the subject eye, and front image data based on fluorescent light from the subject eye.

(24) The ophthalmic analysis device according to any one of (20) to (23), wherein:

the analysis processing means acquires blood vessel density of the capillary area as the measurement result on the capillary area.

(25) The ophthalmic analysis device according to any one of (20) to (24), wherein:

the analysis processing means two-dimensionally or three-dimensionally obtains the measurement result on the capillary area.

(26) The ophthalmic analysis device according to any one of (20) to (25), wherein:

a color map color-coded according to measurement results of individual positions on the capillary area is displayed.

(27) The ophthalmic analysis device according to any one of (20) to (26), further comprising:

a blood vessel information database based on the measurement result on the capillary area acquired through the alleviating process.

(28) An ophthalmic analysis device for analyzing subject eye data including blood vessel information of a subject eye, comprising:

an analysis processing means configured to analyze the subject eye data, thereby acquiring a measurement result on a vascular area included in a specific depth area, wherein the analysis processing means corrects the measurement result on the basis of a measurement range of the depth area.

(29) The ophthalmic analysis device according to (28), wherein:

the subject eye data is OCT front motion contrast data based on three-dimensional motion contrast data of the specific depth area, and on the basis of the measurement range of the depth area, the analysis processing means corrects a two-dimensional measurement result on the vascular area included in the specific depth area.

(30) The ophthalmic analysis device according to (28), wherein:

the fundus data is OCT front motion contrast data of a specific layer area, and on the basis of thickness data on the layer area, the analysis processing means corrects the two-dimensional measurement result on the vascular area included in the specific depth area.

(31) An ophthalmic analysis device for analyzing data acquired by ophthalmic OCT, comprising:

a display control means configured to display a blood vessel analysis map based on OCT motion contrast data acquired by the ophthalmic OCT, and a morphology analysis map based on OCT data acquired by the ophthalmic OCT, on a monitor, at the same time.

(32) The ophthalmic analysis device according to (31), wherein:

the display control means displays the morphology analysis map and the blood vessel analysis map related to a common layer area of a fundus, at the same time.

(33) The ophthalmic analysis device according to (31) or (32), wherein:

the blood vessel analysis map and the morphology analysis map have the property of any one of a basic map, a difference map, a comparison map, and an examination date difference map, and maps having the same property are displayed at the same time.

(34) An ophthalmic analysis device for analyzing data acquired by ophthalmic OCT, comprising:

an analysis processing means configured to perform an integrated measurement process which is a measuring process of integrating a blood vessel measurement result based on OCT motion contrast data acquired by the ophthalmic OCT, and a morphology measurement result based on OCT data acquired by the ophthalmic OCT.

(35) The ophthalmic analysis device according to (34), further comprising:

a display control means configured to display a result of the integrated measurement process as a single color map or analysis chart in a case where each measurement result is acquired as a two-dimensional distribution.

(36) An ophthalmic analysis device for analyzing data acquired by ophthalmic OCT, comprising:

a display control means configured to acquire time-series data which is a blood vessel measurement result based on OCT motion contrast data, from a storage unit, and display the acquired blood vessel measurement result over time.

(37) An ophthalmic analysis device for analyzing OCT motion contrast data including a vascular area of a subject eye, comprising:
an analysis processing means for analyzing the OCT motion contrast data,
wherein the analysis processing means acquires arteriovenous information on the vascular area included in the OCT motion contrast data, and
the arteriovenous information is given to the vascular area.

(38) The ophthalmic analysis device according to (37), wherein:
the analysis processing means acquires the arteriovenous information based on data acquired by OCT.

(39) The ophthalmic analysis device according to (37), wherein:
the analysis processing means acquires the arteriovenous information based on oxygen saturation data on the subject eye.

(40) The ophthalmic analysis device according to (37), wherein:
the analysis processing means acquires the arteriovenous information based on image data acquired by an imaging means different from the OCT.

(41) The ophthalmic analysis device according to any one of (37) to (40), further comprising:
a display control means configured to perform image processing on the OCT motion contrast data on the basis of the acquired arteriovenous information, and display the OCT motion contrast data including the arteriovenous information on a display unit.

(42) The ophthalmic analysis device according to any one of (37) to (41), wherein:
when acquiring a measurement result on a vascular area by analyzing the motion contrast data, the analysis processing means uses the arteriovenous information to acquire at least one of a measurement result on an artery area and a measurement result on a vein area.

(43) The ophthalmic analysis device according to (42), wherein:
the analysis processing means two-dimensionally or three-dimensionally obtains at least one of the measurement result on the artery area and the measurement result on the vein area.

(44) An ophthalmic analysis device for analyzing OCT motion contrast data including a vascular area of a subject eye, comprising:
an analysis processing means for analyzing the OCT motion contrast data,
wherein, with respect to three-dimensional OCT motion contrast data, the analysis processing means calculates edge strengths in three directions, respectively, and acquires running-direction information on the vascular area included in the three-dimensional OCT motion contrast data, on the basis of the edge strengths of the individual directions,
or with respect to three-dimensional OCT motion contrast data, the analysis processing means performs a thinning process with respect to each direction of three directions, and acquires the running-direction information from a skeleton of the thinning process, and
the running-direction information is given to the vascular area.

(45) The ophthalmic analysis device according to (44), wherein:
a display control unit configured to perform image processing on the three-dimensional motion contrast data on the basis of the acquired running-direction information, and display the three-dimensional motion contrast data including the running-direction information on a display unit.

(46). The ophthalmic analysis device according to (44) or (45), wherein:
when analyzing the three-dimensional motion contrast data, thereby acquiring a measurement result on a vascular area, the analysis processing means uses the running-direction information to acquire the degree of tortuosity of blood vessels.

(47) An ophthalmic analysis device for analyzing OCT motion contrast data including a vascular area of a subject eye, comprising:
an analysis processing means for analyzing the OCT motion contrast data,
wherein the analysis processing means acquires layer running information representing a running state of the vascular area included in the OCT motion contrast data with respect to a layer area formed in the subject eye, and
the layer running information is given to the vascular area.

(48) The ophthalmic analysis device according to (47), wherein:
the OCT motion contrast data is OCT motion contrast data on a plurality of layers formed in a fundus of the subject eye, and
the analysis processing means specifies a layer area where the at least one blood vessel runs, among the plurality of layers, and acquires the running-direction information.

(49) The ophthalmic analysis device according to (48), wherein:
on the basis of the running-direction information, the analysis processing means determines whether each blood vessel distributed in a choroid layer reaches a RPE layer.

(50) The ophthalmic analysis device according to any one of (47) to (49), wherein:
the analysis processing means acquires the layer running information on blood vessels crossing a plurality of layers of the motion contrast data.

(51) An ophthalmic analysis device for analyzing OCT motion contrast data including a vascular area of a subject eye, comprising:
an analysis processing means for analyzing the OCT motion contrast data,
wherein the analysis processing means acquires bleeding information on the vascular area included in the OCT motion contrast data, and
the analysis processing means gives the bleeding information to the vascular area.

(52) An ophthalmic analysis device for analyzing OCT motion contrast data including a vascular area of a subject eye, comprising:
an analysis processing means for analyzing the OCT motion contrast data,
wherein the analysis processing means acquires blood vessel information on the vascular area included in the OCT motion contrast data, and
the analysis processing means gives the acquired blood vessel information to the at least one blood vessel data item.

(53) The ophthalmic analysis device according to claim (51), wherein:
the analysis processing means acquires the blood vessel information from OCT data acquired by OCT.

What is claimed is:
1. An ophthalmic analysis device for analyzing OCT motion contrast data including blood vessel information of a subject eye acquired by an ophthalmic OCT, comprising:

a processor; and
memory storing computer readable program, when executed by the processor, causing the ophthalmic analysis device to execute:
an analysis process of analyzing the OCT motion contrast data to acquire a measurement result related to a capillary area of the subject eye; and
a display process of displaying the measurement result related to the capillary area with the OCT motion contrast data,
wherein the analysis process executes an alleviating process for alleviating the influence of great blood vessels having blood vessel diameters larger than those of capillaries on the measurement result to acquire the measurement result related to the capillary area,
wherein the measurement result related to the capillary area is displayed as a numeric value with the OCT motion contrast data, and
wherein the numeric value indicates at least any one of blood vessel density, blood vessel area, a total quantity of blood vessels, a degree of tortuosity of blood vessels, and regularity of blood vessels.

2. The ophthalmic analysis device according to claim 1, wherein:
a process of specifying the capillary area of the OCT motion contrast data is performed as the alleviating process, and
the measurement result related to the capillary area is acquired on the basis of the specified capillary area.

3. The ophthalmic analysis device according to claim 1, wherein:
as the alleviating process, in the OCT motion contrast data, an area surrounded by blood vessels is specified on the basis of a vascular area included in the OCT motion contrast data, and
the measurement result related to the capillary area is acquired on the basis of the specified area.

4. The ophthalmic analysis device according to claim 1, wherein:
at least one of front image data based on reflected light from the subject eye, and front image data based on fluorescent light from the subject eye is analyzed to acquire the measurement result related to the capillary area of the subject eye.

5. The ophthalmic analysis device according to claim 1, wherein
blood vessel density of the capillary area is acquired as the measurement result related to the capillary area.

6. The ophthalmic analysis device according to claim 1, wherein:
the measurement result related to the capillary area is obtained two-dimensionally or three-dimensionally.

7. The ophthalmic analysis device according to claim 1, wherein:
a color map color-coded according to measurement results of individual positions related to the capillary area is displayed.

8. The ophthalmic analysis device according to claim 1, further comprising:
a blood vessel information database based on the measurement result related to the capillary area acquired through the alleviating process.

9. The ophthalmic analysis device according to claim 1, wherein:
the OCT motion contrast data is analyzed, the measurement result related to the vascular area included in a specific depth area is acquired, and the measurement result is corrected on the basis of a measurement range of the depth area.

10. The ophthalmic analysis device according to claim 1, wherein:
a blood vessel analysis map based on the OCT motion contrast data acquired by the ophthalmic OCT, and a morphology analysis map based on the OCT data acquired by ophthalmic OCT are displayed on a monitor at the same time.

11. The ophthalmic analysis device according to claim 1, wherein:
an integrated measurement process of integrating a blood vessel measurement result based on the OCT motion contrast data acquired by ophthalmic OCT, and a morphology measurement result based on OCT data acquired by ophthalmic OCT is performed.

12. The ophthalmic analysis device according to claim 1, wherein:
time-series data which is a blood vessel measurement result based on the OCT motion contrast data is acquired from a storage unit, and the acquired blood vessel measurement result is displayed over time.

13. The ophthalmic analysis device according to claim 1, wherein:
arteriovenous information on the vascular area included in the OCT motion contrast data is acquired, and the arteriovenous information is given to the vascular area.

14. The ophthalmic analysis device according to claim 13, wherein:
the arteriovenous information based on data acquired by ophthalmic OCT is acquired.

15. The ophthalmic analysis device according to claim 1, wherein:
the subject eye data is three-dimensional OCT motion contrast data, and
edge strengths with respect to three-dimensional OCT motion contrast data are calculated in three directions, respectively to acquire running-direction information on the vascular area included in the three-dimensional OCT motion contrast data on the basis of the edge strengths of the individual directions, or a thinning process with respect to three-dimensional OCT motion contrast data is performed with respect to each direction of three directions to acquire the running-direction information from a skeleton of the thinning process, and
the running-direction information is given to the vascular area.

16. The ophthalmic analysis device according to claim 1, wherein:
layer running information representing a running state of a vascular area included in the OCT motion contrast data with respect to a layer area formed at the subject eye is acquired, and
the layer running information is given to the vascular area.

17. The ophthalmic analysis device according to claim 16, wherein:
bleeding information on the vascular area included in the OCT motion contrast data is acquired, and the bleeding information is given to the vascular area.

18. The ophthalmic analysis device according to claim 1, wherein:
the numeric value is displayed to be overlaid on the OCT motion contrast data.

19. An ophthalmic analysis device for analyzing OCT motion contrast data including a vascular area of a subject eye, comprising:

a processor; and memory storing a computer readable program, when executed by the processor, causing the ophthalmic analysis device to execute:

an analysis process of analyzing the OCT motion contrast data to acquire arteriovenous information on the vascular area included in the OCT motion contrast data; and a display process of displaying the arteriovenous information with the OCT motion contrast data, wherein the arteriovenous information is given to the vascular area.

20. The ophthalmic analysis device according to claim 19, wherein:

the analysis process acquires the arteriovenous information based on data acquired by OCT.

21. An ophthalmic analysis device for analyzing OCT motion contrast data including blood vessel information of a subject eye acquired by an ophthalmic OCT, comprising:

a processor; and memory storing computer readable program, when executed by the processor, causing the ophthalmic analysis device to execute:

an analysis process of analyzing the OCT motion contrast data to acquire a measurement result related to a capillary area of the subject eye; and a display process of displaying the measurement result related to the capillary area with the OCT motion contrast data, wherein the analysis process executes an alleviating process for alleviating the influence of great blood vessels having blood vessel diameters larger than those of capillaries on the measurement result to acquire the measurement result related to the capillary area, wherein:

a color map color-coded according to measurement results of individual positions related to the capillary area is displayed, and the color map is displayed with the OCT motion contrast data.

22. The ophthalmic analysis device according to claim 21, wherein:

the color map is displayed to be overlaid on the OCT motion contrast data.

* * * * *